(12) United States Patent
Rubinstenn et al.

(10) Patent No.: US 7,324,668 B2
(45) Date of Patent: Jan. 29, 2008

(54) FEATURE EXTRACTION IN BEAUTY ANALYSIS

(75) Inventors: Gilles Rubinstenn, Paris (FR); Francis Pruche, Senlis (FR)

(73) Assignee: L'Oreal S.A., Paris (FR)

( * ) Notice: Subject to any disclaimer, the term of this patent is extended or adjusted under 35 U.S.C. 154(b) by 1035 days.

(21) Appl. No.: 10/024,495

(22) Filed: Dec. 21, 2001

(65) Prior Publication Data

US 2003/0063801 A1 Apr. 3, 2003

Related U.S. Application Data

(60) Provisional application No. 60/325,559, filed on Oct. 1, 2001.

(51) Int. Cl.
*G06K 9/00* (2006.01)
*G06K 9/46* (2006.01)
*G06K 9/66* (2006.01)
*G06K 9/36* (2006.01)

(52) U.S. Cl. .................. 382/118; 382/190; 382/276

(58) Field of Classification Search ............ 382/100, 382/118, 190, 195, 203, 276, 128; 345/646
See application file for complete search history.

(56) References Cited

U.S. PATENT DOCUMENTS

| | | | | |
|---|---|---|---|---|
| 3,030,967 A | * | 4/1962 | Peyron | 132/333 |
| 4,253,086 A | * | 2/1981 | Szwarcbier | 382/126 |
| 4,894,547 A | * | 1/1990 | Leffell et al. | 250/461.2 |
| 5,016,173 A | * | 5/1991 | Kenet et al. | 382/128 |
| 5,308,609 A | * | 5/1994 | Etheredge, III | 424/61 |
| 5,363,854 A | * | 11/1994 | Martens et al. | 356/390 |
| 5,751,829 A | | 5/1998 | Ringland et al. | 382/100 |
| 5,760,407 A | * | 6/1998 | Margosiak et al. | 250/461.2 |
| 6,091,836 A | | 7/2000 | Takano et al. | 382/118 |
| 6,208,749 B1 | * | 3/2001 | Gutkowicz-Krusin et al. | 382/128 |
| 6,260,024 B1 | | 7/2001 | Shkedy | 705/37 |
| 6,293,284 B1 | | 9/2001 | Rigg | 132/200 |
| 6,571,003 B1 | * | 5/2003 | Hillebrand et al. | 382/118 |
| 2001/0011818 A1 | | 8/2001 | Dockery et al. | 281/15.1 |
| 2001/0014868 A1 | | 8/2001 | Herz et al. | 705/14 |
| 2002/0024528 A1 | * | 2/2002 | Lambertsen | 345/646 |
| 2002/0054714 A1 | | 5/2002 | Hawkins et al. | 382/276 |

FOREIGN PATENT DOCUMENTS

EP 0 226 959 7/1987

(Continued)

OTHER PUBLICATIONS

Lievin et al., "Lip features Automatic Extraction", Oct. 1998, IEEEICIP 98, vol. 3, pp. 168-172.*

(Continued)

*Primary Examiner*—Bhavesh M. Mehta
*Assistant Examiner*—Manav Seth
(74) *Attorney, Agent, or Firm*—Finnegan, Henderson, Farabow, Garrett & Dunner, L.L.P.

(57) ABSTRACT

A method of performing a beauty analysis is disclosed. The method comprises receiving information of at least one portion of a subject's external body condition, identifying in the information at least one condition, extracting from the information at least one feature of the at least one condition, and storing extracted information reflective of the at least one feature.

36 Claims, 14 Drawing Sheets

FOREIGN PATENT DOCUMENTS

| | | |
|---|---|---|
| EP | 1 030 267 | 8/2000 |
| EP | 1 134 701 | 9/2001 |
| EP | 1 169 964 | 1/2002 |
| EP | 1 177 766 | 2/2002 |
| JP | A 05-263411 | 10/1993 |
| JP | A 06-105826 | 4/1994 |
| JP | 06-189942 | 7/1994 |
| JP | A 07-093549 | 4/1995 |
| JP | 07-231883 | 9/1995 |
| JP | 09-051525 | 2/1997 |
| JP | A 2001-419 | 1/2001 |
| JP | 2001-314376 | 11/2001 |
| JP | 2001-344345 | 12/2001 |
| WO | WO 98/20458 | 5/1998 |
| WO | WO 99/23609 | 5/1999 |
| WO | WO 00/33271 | 6/2000 |
| WO | WO 00/76398 | 12/2000 |
| WO | WO 01/04838 | 1/2001 |
| WO | WO 01/04840 | 1/2001 |
| WO | WO 01/18674 | 3/2001 |
| WO | WO 01/20517 | 3/2001 |
| WO | WO 01/35827 | 5/2001 |
| WO | WO 01/57771 | 8/2001 |
| WO | WO 01/77976 | 10/2001 |
| WO | WO 01/80122 | 10/2001 |
| WO | WO 01/87245 | 11/2001 |
| WO | WO 01/91600 | 12/2001 |
| WO | WO 01/91601 | 12/2001 |
| WO | WO 02/03232 | 1/2002 |
| WO | WO 02/05249 | 1/2002 |
| WO | WO 02/37421 | 5/2002 |

OTHER PUBLICATIONS

Environmental Health Criteria 160 (EHC 160), 1994, 2nd edition, "Ultraviolet radiation". (pp. 1-4, 45-47).*

Yin Wu, et al., "A Plastic-Visco-Elastic Model for Wrinkles in Facial Animation and Skin Aging", MIRALab, 1998, 10 pages.

Catherine Pelachaud, et al., "Final Report to NSF of the Standards for Facial Animation Workshop", The Institute For Research In Cognitive Science, University of Pennsylvania, IRCS Report 94-21, Nov. 1994, pp. 1-62.

Co-pending U.S. Appl. No. 10/024,354; Title: Methods and Systems for Predicting and/or Tracking Changes in External Body Conditions, Inventor(s): Gilles Rubinstenn et al., filed: Dec. 21, 2001, Preliminary Amendment Filed Apr. 22, 2002.

Co-pending U.S. Appl. No. 10/024,333; Title: Methods and Systems for Generating a Prognosis, Inventor(s): Gilles Rubinstenn et al., Filed: Dec. 21, 2001, Preliminary Amendment Filed: April 22, 2002.

Co-pending U.S. Appl. No. 10/024,622; Title: Historical Beauty Record, Inventor(s): Daniela Giacchetti et al., Filed: Dec. 21, 2001, Preliminary Amendment Filed: Apr. 22, 2002.

Co-pending U.S. Appl. No. 10/024,332; Title Identification and Presentation of Analogous Beauty Case Histories, Inventor(s): Gilles Rubinestenn, Filed: Dec. 21, 2001, Preliminary Amendment Filed: Apr. 22, 2002.

Co-pending U.S. Appl. No. 10/024,481; Title: Interactive Beauty Analysis, Inventor(s): Gilles Runinstenn et al., filed Dec. 21, 2001, Preliminary Amendment Filed: Apr. 22, 2002.

Co-pending U.S. Appl. No. 10/024,353; Title: Simulation of an Aesthetic Feature on a Facial Image, Inventor(s): Daniela Giacchetti et al., filed Dec. 21, 2001, Preliminary Amendment Filed: Apr. 22, 2002.

Co-pending U. S. Appl. No. 10/024,496; Title: Beauty Advisory System and Method, Inventor(s): Gilles Rubinstenn et al., filed Dec. 21, 2001, Preliminary Amendment Filed: Apr. 22, 2002.

Co-pending U. S. Appl. No. 10/024,620; Title: Virtual Beauty Consultant, Inventor(s): Daniela Giacchetti et al., filed Dec. 21, 2001, Preliminary Amendment Filed: Apr. 22, 2002.

Co-pending U. S. Appl. No. 10/024,334; Title: Calibrating image Capturing Inventor(s): Gilles Rubinstenn, filed Dec. 21, 2001, Preliminary Amendment Filed: Apr. 22, 2002.

Co-pending U.S. Appl. No. 10/024,616; Title: Use of Artifical Intelligence in Providing Beauty Advice, Inventor(s): Jerome Peyrelevade, filed Dec. 21, 2001, Preliminary Amendment Filed: Apr. 22, 2002.

Co-pending U.S. Appl. No. 10/024,352; Title: Shop-in-Shop Website Construction, Inventor(s): Jerome Peyrelevade et al., filed Dec. 21, 2001.

Co-pending U.S. Appl. No. 10/024,619; Title: Early Detection of Beauty Treatment Progress, inventor(s): Francis Pruche et al., filed: Dec. 21, 2001, Preliminary Amendment Filed: Apr. 22, 2002.

Co-pending U.S. Appl. No. 10/024,356 ; Title: Cosmetic Affinity Indexing, Inventor(s): Daniela Giacchetti et al., filed: Dec. 21, 2001.

Co-pending U.S. Appl. No. 10/024,621; Title: Systems and Methods for Providing Beauty Guidance, Inventor(s): Daniela Giacchetti et al., filed: Dec. 21, 2001,Preliminary Amendment Filed: Apr. 22, 2002.

Co-pending U.S. Appl. No. 10/024,355; Title: Methods and Systems Involving Simulated Application of Beauty Product, Inventor(s): Jerome Peyrelevade et al., filed: Dec. 21, 2001, Preliminary Amendment Filed: Apr. 22, 2002.

Co-pending U.S. Appl. No. 10/024,351; Title: Customized Beauty Tracking Kit, Inventor(s): Gilles Rubinstenn et al., filed Dec. 21, 2001, Preliminary Amendment Filed: Apr. 22, 2002.

Co-pending U.S. Appl. No. 10/024,615; Title: Analysis Using a Three-Dimensional Facial Image, Inventor(s): Gilles Rubinstenn et al., filed Dec. 21, 2001, Preliminary Amendment Filed: Apr. 22, 2002.

Co-pending U.S. Appl. No. 10/024,482; Title: Body Image Templates With Pre-Applied Beauty Products, Inventor(s): Daniela Giacchetti, filed Dec. 21, 2001, Preliminary Amendment Filed: Apr. 22, 2002.

Co-pending U.S. Appl. No. 10/024,651; Title: Image Capture Method, Inventor(s): Gilles Rubinstenn, filed Dec. 21, 2001, Preliminary Amendment Filed: Apr. 22, 2002.

Co-pending U.S. Appl. No. 10/024,034; Title: Devices and Methods for Enabling Evaluation of Typological Characteristics of External Body Portions, and Related Devices, Inventor(s): Roland Bazin, filed Dec. 21, 2001.

Co-pending U.S. Appl. No. 10/024,480; Title: Body Image Enhancement, Inventor(s): Gilles Rubinstenn et al., filed Dec. 21, 2001, Preliminary Amendment filed: Apr. 22, 2002.

* cited by examiner

WRINKLE DATA

| REGION | FREQUENCY | INTENSITY |
|---|---|---|
| CHIN | 0 | 0 |
| UPPER LIP | 0 | 0 |
| CHEEKS | 4.1 | 3.2 |
| EYES | 3.1 | 1.2 |
| FOREHEAD | 0 | 0 |
| OVERALL | 2.3 | 1.4 |

ANALYSIS 1/1/01

FEATURE EXTRACTION IN BEAUTY ANALYSIS

This application claims priority to U.S. provisional application No. 60/325,559, filed Oct. 1, 2001.

BACKGROUND OF THE INVENTION

1. Field of the Invention

The present invention relates to methods, combinations, apparatus, systems, and articles of manufacture involving feature extraction in beauty analysis. The invention may be particularly beneficial for extracting from images and isolating for analysis skin, hair, and nail conditions such as wrinkles, freckles, split-ends, nail discoloration and other conditions.

2. Description of Related Art

Beauty treatments, and particularly treatments of the facial skin, are often aimed at improving a particular skin condition. For example, a subject with a condition such as wrinkles may seek a treatment focused on wrinkle reduction while a subject with a condition such as freckles may seek a treatment specifically tailored to reducing the frequency and intensity of freckles. In both instances, it may be beneficial to quantify the extent of the adverse conditions at the beginning of the treatment and at various stages during the treatment in order to gauge treatment effectiveness and/or to help the subject better appreciate the extent of the adverse condition. Further, quantification of conditions is often helpful in determining an appropriate treatment regimen.

SUMMARY OF A FEW ASPECTS OF THE INVENTION

Methods, combinations, apparatus, systems, and articles of manufacture consistent with the features and principles of the present invention may perform feature extraction in beauty analysis.

One exemplary aspect of the present invention may include a method of performing a skin, hair, or nail analysis. The method may include receiving at least one image of at least one portion of a subject's facial skin, identifying in the at least one image at least one skin, hair, or nail condition, extracting from the at least one image at least one representation of the at least one skin, hair, or nail condition, and storing information reflective of the at least one representation.

A second exemplary aspect may further include quantifying the at least one representation. The quantification may indicate at least one of an extent, intensity, frequency, type, and severity of the at least one skin, hair, or nail condition.

In a third exemplary aspect, a facial image may be processed to substantially identify all visible occurrences of the at least one skin, hair, or nail condition in at least one part of the at least one portion of the subject. This process may result in at least one representation of the skin, hair, or nail condition substantially devoid of all subject-identifying features other than the condition.

A fourth exemplary aspect of the present invention may include receiving an image of a portion of a subject's skin, identifying in the image at least one skin condition, extracting from the image at least one representation of the at least one skin condition, and storing information reflective of the at least one representation.

A fifth exemplary aspect of the present invention may include a system for performing a skin, hair, or nail analysis. The system may include first memory for storing an image of at least a portion of a subject, a processor(s) configured to identify in the image at least one skin, hair, or nail condition and for extracting from the image at least one representation of the at least one skin, hair, or nail condition, and second memory for storing information reflective of the at least one representation. Of course, the first and second memories might exist within the same physical structure.

Additional aspects of the invention are set forth in the description which follow and, in part, are obvious from the description, or may be learned by practice of methods, combinations, devices, systems, and articles of manufacturer consistent with features of the present invention. The aspects of the invention may be realized and attained by means of the elements and combinations particularly pointed out in the appended claims. It is understood that both the foregoing description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several aspects of the invention and, together with the description, serve to explain exemplary principles of the invention. In the drawings.

DESCRIPTION OF EXEMPLARY EMBODIMENTS

Reference is now made in detail to exemplary embodiments of the invention, examples of which are illustrated in the accompanying drawings. Wherever possible, the same reference numbers are used throughout the drawings to refer to the same or like parts. While the invention has particular benefit with respect to skin, hair, and nail analysis, the foregoing description uses skin analysis for exemplary purposes.

One embodiment of the invention may include a method for performing a skin analysis. Consistent with the invention, the skin analysis may include identifying and/or quantifying a skin condition. Examples of skin conditions may include skin texture, elasticity, dryness, cellulitis, sweating, aging, wrinkles, melanoma, exfoliation, desquamation, homogeneity of color, micro-circulation, shininess, softness, smoothness, hydration, sebum production, cleanliness, irritation, redness, vasomotion, vasodilation, vasoconstriction, pigmentation, freckles, or any other visible condition affecting the skin.

Figure 1:
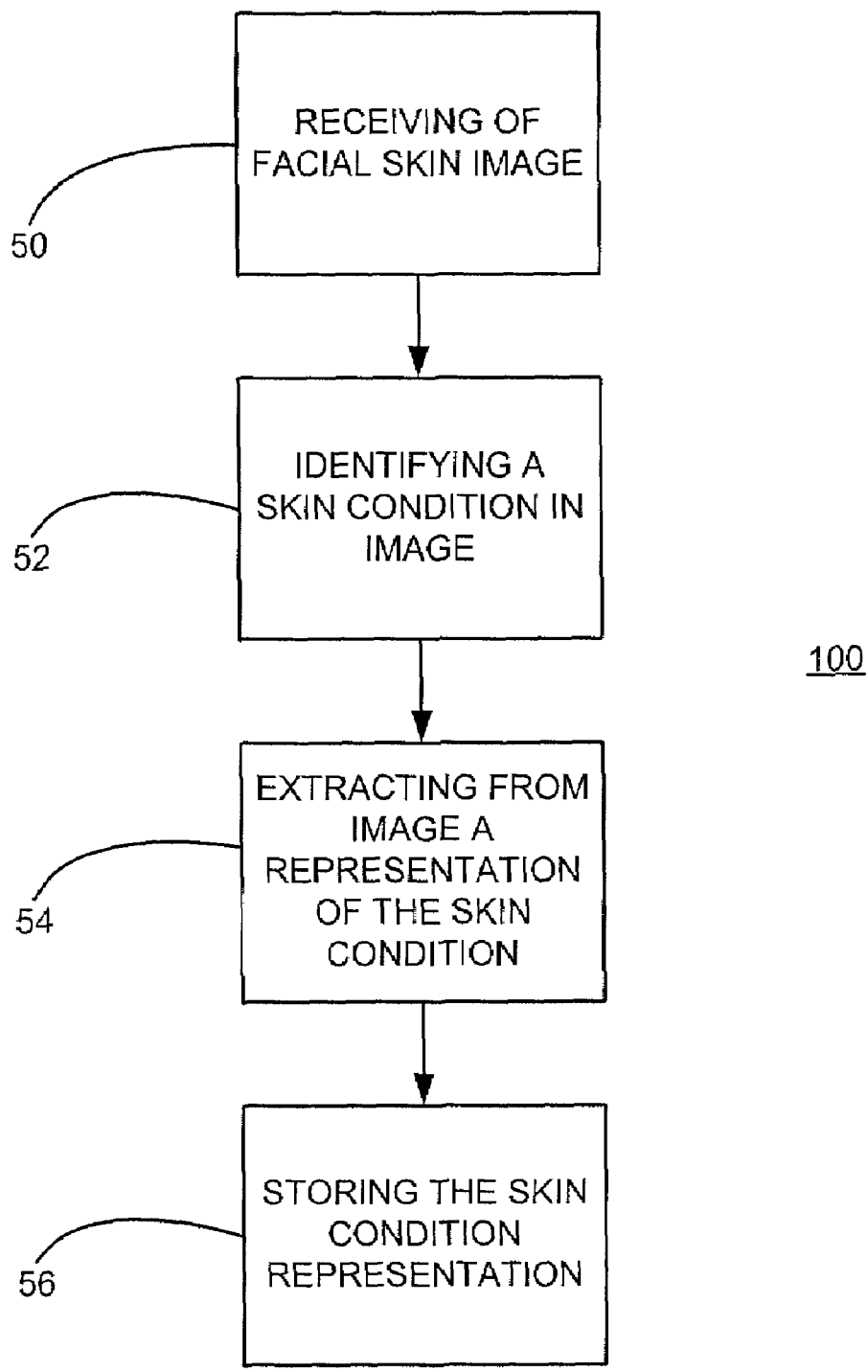
FIG. 1 illustrates an exemplary flow chart for performing skin analysis consistent with features and principles of the present invention.

An embodiment of the invention may also include receiving an image of at lease one portion of a subject's facial skin. Consistent with the invention, the image may include an image of the entire face of the subject or a portion of the subject's face. Images may contain detailed pictures of the subject's facial skin or images may contain topological plots mapping the contours of the subject's facial skin. As illustrated in a flow chart of FIG. 1, a facial skin image may be received at block 50 through one of many mechanisms. Although mechanisms for capturing the facial image are not necessarily a part of the invention in its broadest sense, the image may be captured by a web camera, film camera, analog camera, digital camera, scanner, ultra-sound imaging device or any other mechanism for acquiring a representation of the subject's countenance. The image may be received electronically or physically. Examples of electronic means for receiving a facial image include reception over a network, reception on a storage medium, facsimile reception or reception in physical form.

Examples of networks that may be used to receive a facial image include public networks such as the Internet, telephony networks, courier networks (e.g. postal service, United Parcel Service, Federal Express, etc.), private networks, virtual private networks, local area networks, metropolitan area networks, wide area networks, ad hoc networks, or any other mechanism for permitting communication between remote sites, regardless of whether the connection is wired or wireless. In a broader sense, images may be received physically such as in hard copy form, mailed or otherwise couriered to the receiver.

Figure 2:
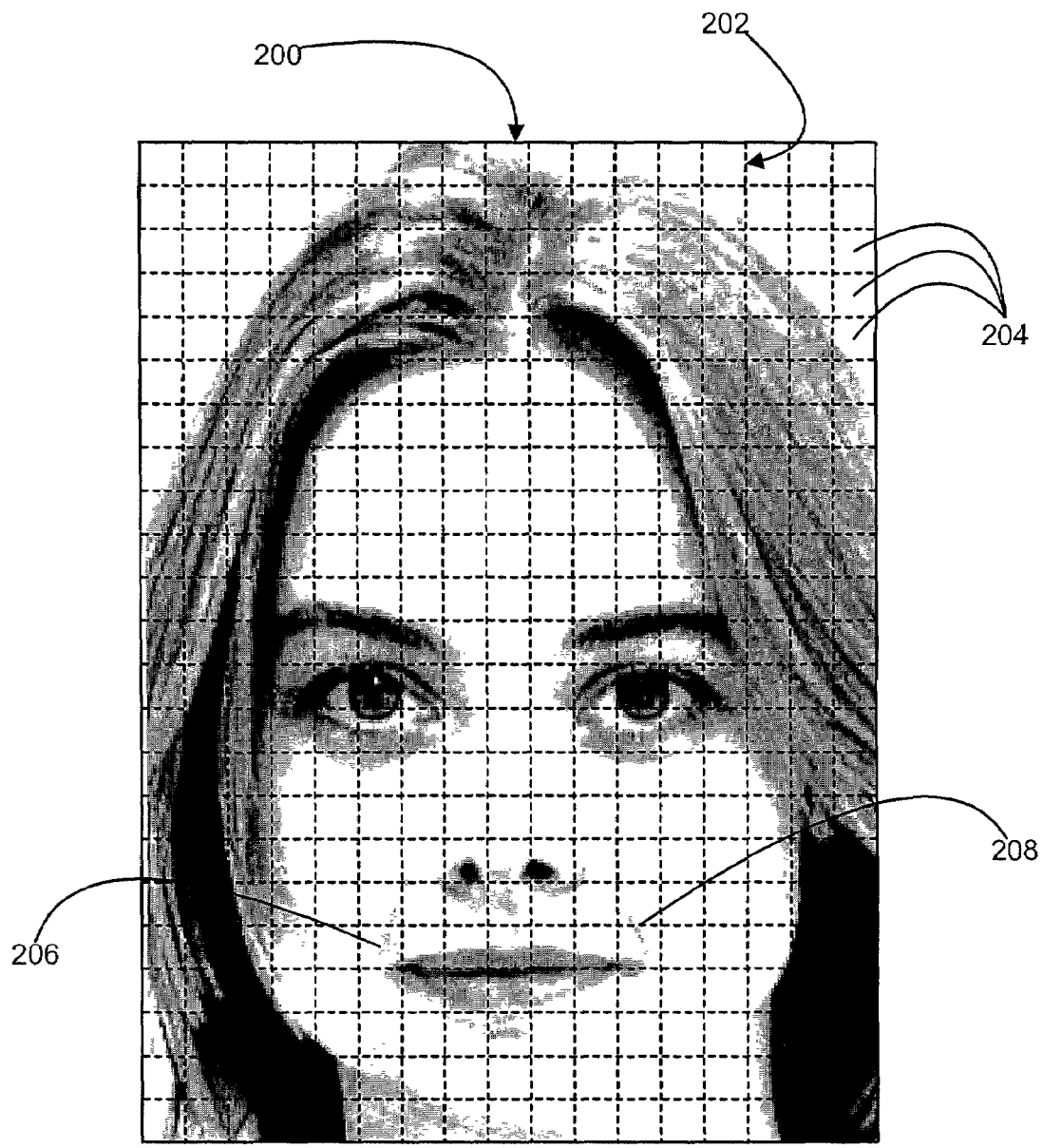
FIG. 2 illustrates an exemplary partitioned image consistent with features and principles of the present invention.

Also consistent with the invention, a method may include identifying in the image at least one skin condition. An exemplary implementation of this step is graphically depicted at block 52 in FIG. 1. The skin condition may be one or more of the conditions previously discussed and may be identified through an image processing technique. Image processing techniques may include a software program, computer, application specific integrated circuit, electronic device and/or a processor designed to identify in an image one or more occurrences of a skin condition. Various image processing algorithms known to persons of ordinary skill in the art of image processing may be employed to identify one or more occurrences of the skin condition in the facial image. These techniques may, for example, use software that processes the facial image to create a partitioned image 200, as is exemplified in FIG. 2. In the partitioned image 200, dotted lines 202 are used to depict how the facial image may be segmented into component parts 204. Image recognition techniques known in the art may analyze each component part 204 to identify conditions such as wrinkles 206 and 208.

Figure 3C:
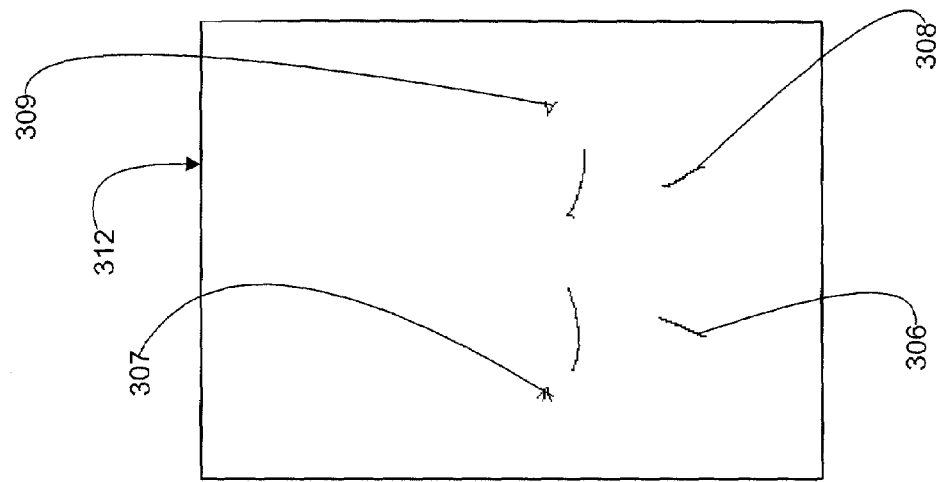
FIG. 3C illustrates an exemplary image with some facial features removed consistent with features and principles of the present invention.
Figure 3B:
FIG. 3B illustrates an exemplary processed image consistent with features and principles of the present invention.
Figure 3A:
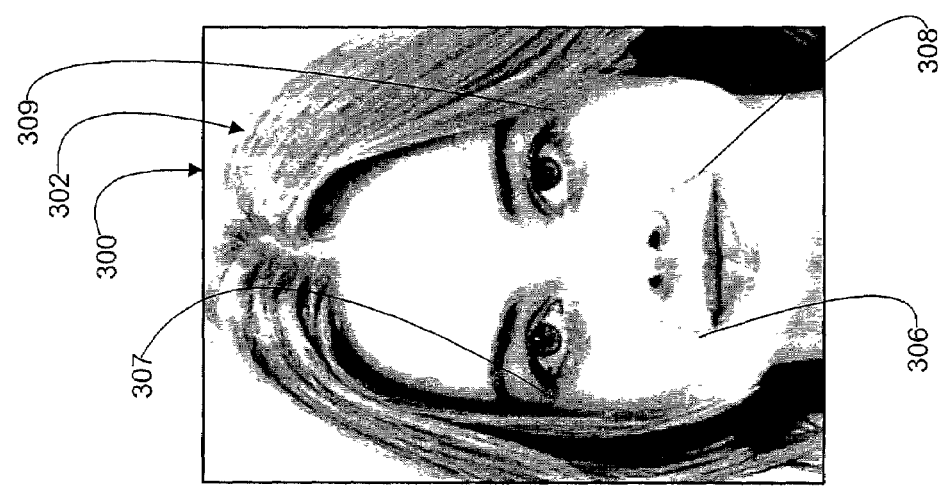
FIG. 3A illustrates an exemplary initial facial image consistent with features and principles of the present invention.

A visual example of how the image processing may work with respect to wrinkle identification is illustrated in FIGS. 3A and 3B. FIG. 3A illustrates an initial facial image 300 of a subject 302. As illustrated, the image reflects wrinkles in the subject's right and left cheek regions 306 and 308 and in regions of the subject's right and left eyes 307 and 309. In FIG. 3B, the image 300 has been processed and the wrinkles 306-309 identified with lines, the shapes of which may represent the contours of the identified wrinkles, and the intensity of which may represent the depth of the wrinkles. While the identification is graphically depicted in FIG. 3B, a graphical depiction is not necessarily a requirement of the invention in its broadest sense. Rather, the identification may occur within a processor. Examples of such processors may include computers, application specific integrated circuits, electronic devices, and any device that may perform identification operations according to prescribed instructions.

Consistent with the invention a method may further include extracting from the image at least one representation of the skin condition. A corresponding step is illustrated at block 54 in FIG. 1. Extraction of representations may occur in one of many ways. For example, as illustrated in FIG. 3C, extraction may occur using image processing to extract from the facial image 310 a skin condition such as wrinkles 306-309. Vice versa, extraction may also occur using image processing to extract from the facial image 310 everything except the skin condition 306-309. Extraction may occur to an extent such that representations may be maintained or transmitted in a compact form. Extraction may also occur to an extent such that the subject is anonymous when the extracted representation is viewed. This may be used to ensure privacy of a subject undergoing a skin analysis. This may result in an image 312 of the skin condition 306-309 with some or all of the facial features removed as depicted in FIG. 3C. The image 312 may be super-imposed on a model to provide a simulation of the skin condition 306-309 without subject-identifiable body portions or invading the subject's privacy.

Examples of techniques relating to processing of images for use in simulating beauty products are disclosed in PCT Publication No. WO 01/77976, published Oct. 18, 2001, the disclosure of which is incorporated herein by reference. Software for such processing is also available from EZ-Face™ of Israel.

Techniques for locating features in an image are known in the art. For example, the image may be binarized to aid in locating features such as wrinkles. Binarization essentially increases the contrast of the image and facilitates feature detection. Fourier transforms, fast Fourier transforms (FFTs), and/or discrete cosine transforms may be performed on all or part of the image, resulting in coefficients. Based on the coefficients, features may be located, as known in the art. Neural networks may also be used to identify features. It is know to persons skilled in the art how to train a neural network to accomplish these functions. Alternatively, one or more digital filters may be passed through the image for locating specific features. These examples are provided for illustrative purposes with the understanding that any image processing technique may be used within the scope and spirit of the invention.

Furthermore, extraction may involve magnifying portions of the image to facilitate identification of skin conditions. Magnification may be performed digitally on a computer or using analog methods such as zooming with an optical lens. Extraction may also involve applying powder to portions of the subject's skin for easier identification of the skin condition. For example, dusting of colored powder may be brushed on a skin condition such as wrinkles to highlight the skin condition. The colored powder may adhere to or fall into wrinkles on the subject's skin, thereby accentuating the wrinkles for identification. Extraction may additionally involve illuminating a portion of the subject's skin with an ultraviolet lamp, such as a Woods lamp. The ultraviolet lamp may help identify an amount of acne-causing bacteria on the portion of the subject's skin by making visible on the subject's skin residues, such as porphyrine, excreted by the bacteria. An image of the illuminated residue may then be captured for image processing.

Figures 4A, 4B:
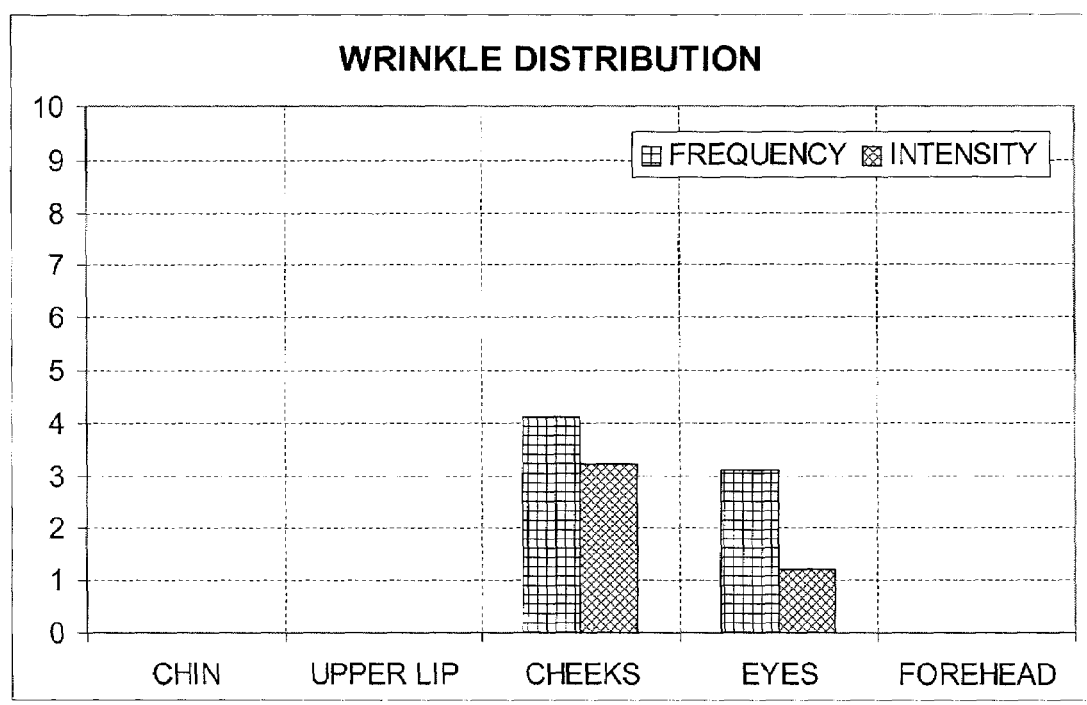
FIG. 4A illustrates an exemplary quantification consistent with features and principles of the present invention.
FIG. 4B illustrates an exemplary graphical representation of quantified data consistent with features and principles of the present invention.
Figure 4C:
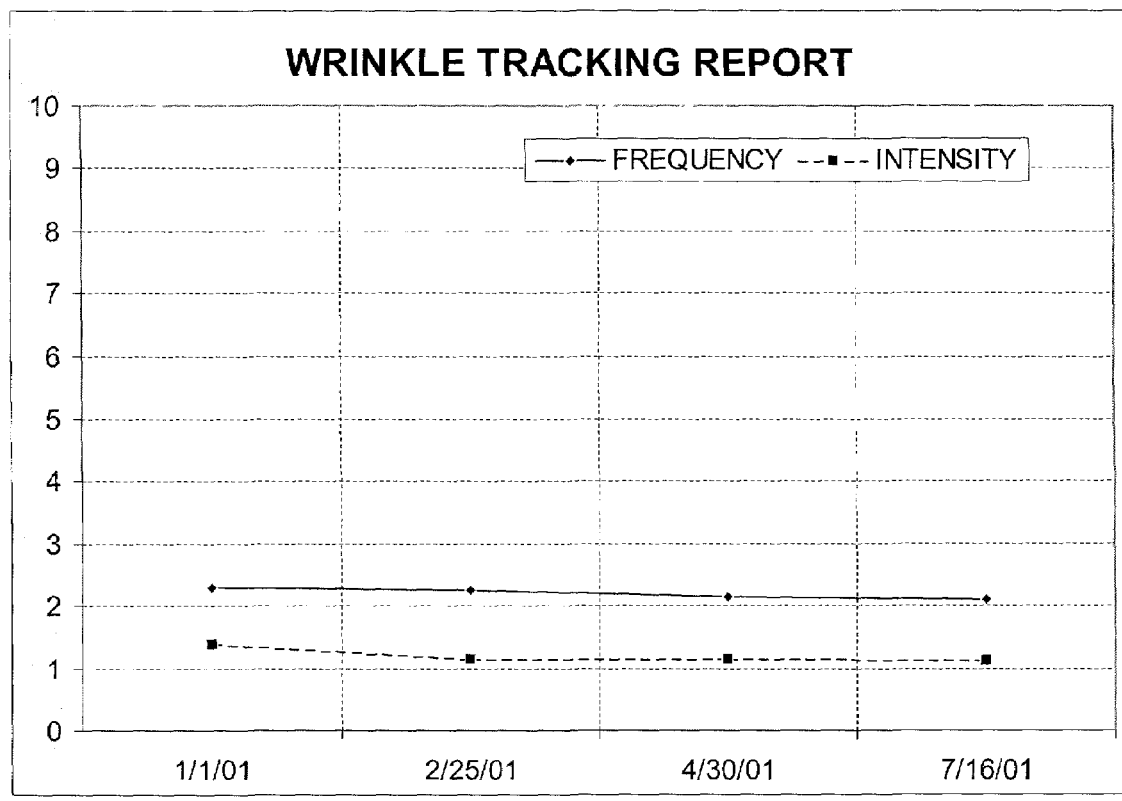
FIG. 4C illustrates an exemplary graph conveying changes in condition consistent with features and principles of the present invention.

Alternatively, the information may be extracted in non-image form, such as through graphical or statistical representation. This concept is exemplified in FIGS. 4A to 4C. In FIG. 4A, the representation of the skin condition occurs numerically with quantifiers characterizing the frequency and severity of a skin condition. As illustrated, an overall analysis may be provided as well as analysis divided by facial region. FIG. 4B exemplifies a graphical representation of the data presented in FIG. 4A. Assuming a subject repeats the analysis process periodically, FIG. 4C is an example of how extracted representations in numeric form may be presented graphically in order to convey to the subject changes in the subject's condition over time. The invention may further permit the subject to record any beauty treatment regimen followed by the subject and to associate the treatment regimen with points on the graph. Such an alternative embodiment may enable the subject to correlate specific treatment regimens and/or products with progress being made in order to gauge effectiveness.

An embodiment consistent with the invention may also include storing information reflective of extracted information. This step is exemplified by block 56 in the flow chart 100 of FIG. 1. In its broadest sense storing may involve maintaining information in memory for a time period sufficient to enable the information to be displayed to the subject. In a narrower respect, storing may include maintaining the information in a memory device for a predetermined or indefinite period of time. Although not part of the invention in its broadest sense, images may be stored in active memory such as RAM, may be stored on a storage medium, or may be stored in any other form. Examples of storage medium may include magnetic storage devices such as floppy disks and hard drives, optical storage devices, such as compact discs and digital video discs, organic storage devices, random access memory, printed media or any other medium for storing information.

Figure 5:
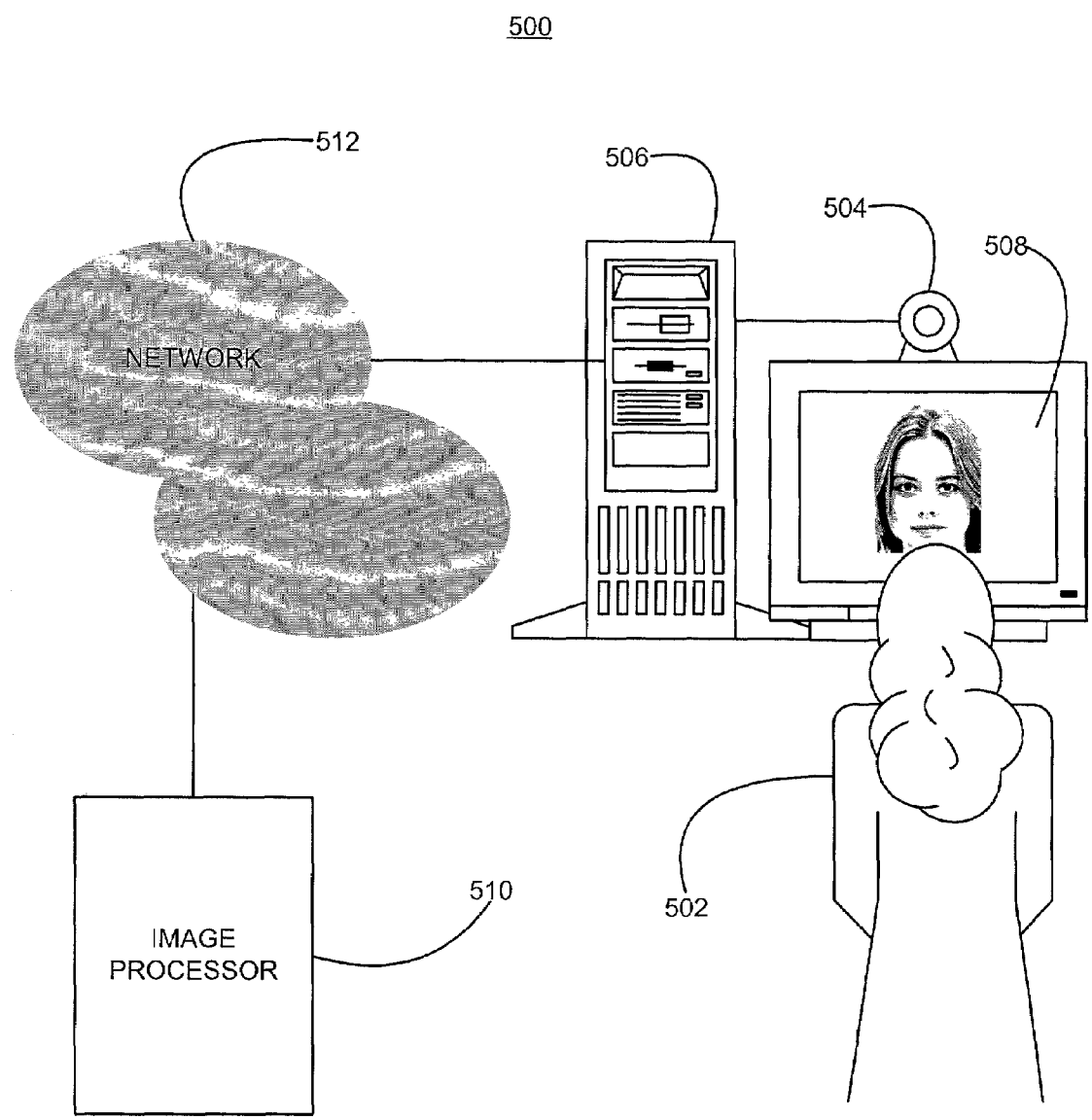
FIG. 5 illustrates an exemplary environment consistent with features and principles of the present invention.
Figure 6:
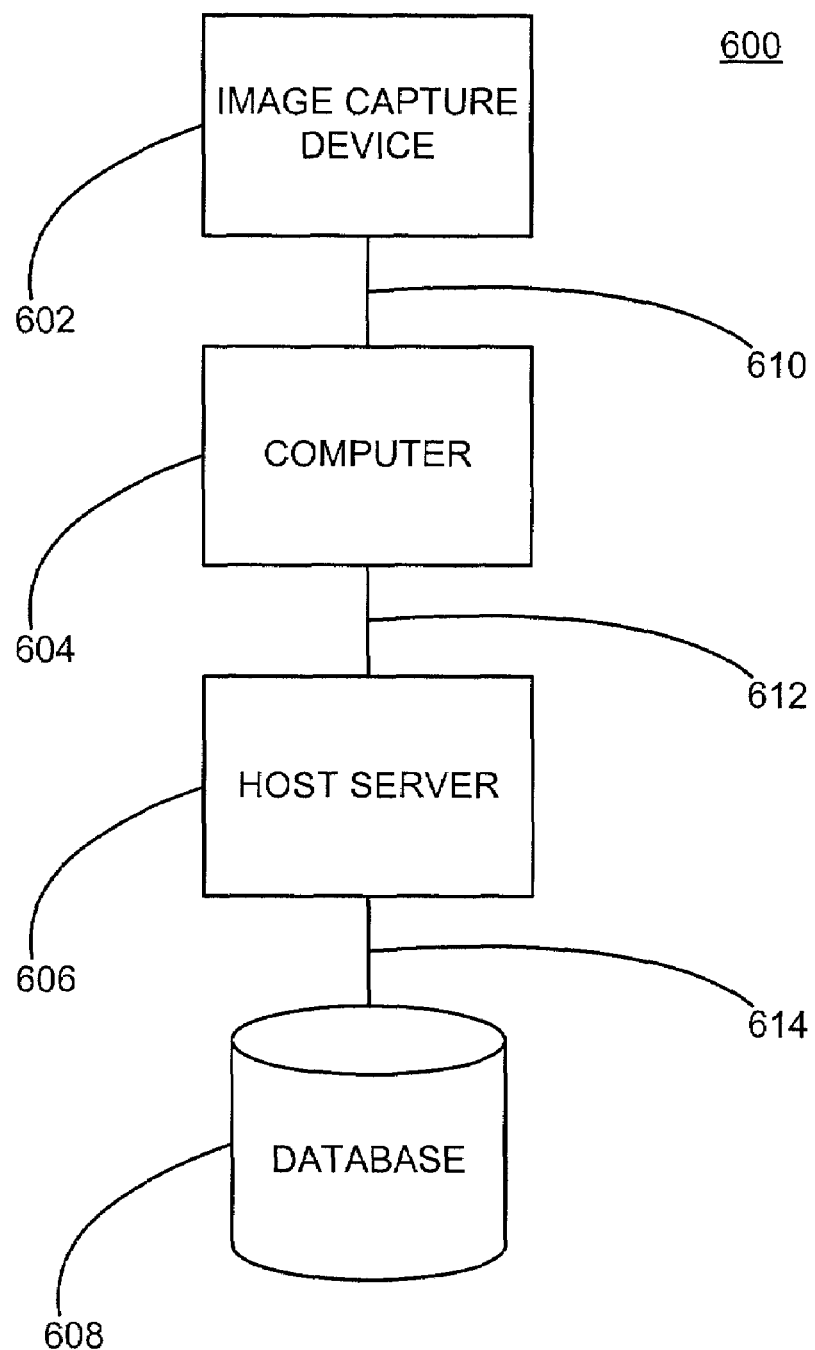
FIG. 6 illustrates an exemplary system consistent with features and principles of the present invention.

As is described hereafter in connection with FIGS. 5 and 6, the information may be stored on a client side of a network, on a server or processor side of a network, or at any location connected to a network. Examples of networks may include the ones previously discussed herein. Alternatively, the information may be stored within a non-networked system. In a broader sense, the information stored may be an image or representation of the extracted skin condition, such as illustrated in FIG. 3C. Alternatively, the stored information may be information derived from the image processing, such as the data reflected in FIGS. 4A to 4C.

FIG. 5 illustrates an exemplary environment 500 in which the invention may be implemented. A subject 502 may self-capture a facial image using a camera such as web camera 504 connected to a central processing unit 506. An interconnected display device 508 may permit the subject to view a captured image. This "subject side" or "client side" structure may be embodied within a home computing system, may be located in a kiosk, or may be part of a processing system run by professionals in a salon, place of business, or retail establishment. The system capturing the image may be linked to an image processor 510 via a network 512. Networks include the examples previously described above. All of the image processing functions may be accomplished in the image processor 510, or may be partially accomplished in the central processing unit 506. Alternatively, and as depicted in FIG. 6, the invention may be implemented in a non-networked system 600.

System 600 may include image capture device 602 (such as web cam, digital camera, etc.), computer 604, host server 606, searchable database 608, and three communication links 610-612. The communication links may be hard wired, wireless, or may include at least one network. Image capture device 602 may be operated by the subject (or at the subject's direction) to obtain image information. Instructions displayed via computer 604 may facilitate the image capture process. The image information may then be relayed to the computer 604 using the first communication link 610. This relay may occur in digital or analog form. The subject may then indicate the skin condition for the computer to analyze. Alternatively, the computer may automatically identify conditions that are beyond a predetermined or given severity. The computer 604 may then process the image to extract and quantify specific skin conditions. Results of extraction, processing, and quantification may thereafter be displayed to the subject in one form or another. Displayed results may include representations of the features to the subject such as the exemplary images 1100, 1200, and 1300 illustrated in FIGS. 11 to 13 and/or statistical and graphical representations such as illustrated in FIGS. 4A to 4C. Results may also include demographic statistics calculated from beauty analyses of other people, including the subject.

Via the computer 604 personal information may be gathered from the subject. The computer 604 may then send some or all of the personal information, image, and features to the host server 606 via the second communications link 612. The host server 606 may receive the sent personal information in the database 608 via the third communications link 614. Unique information that identifies the subject associated with the portions may be retained at computer 604, or if transmitted therefrom, excluded from storage into the database 608 for privacy reasons. Alternatively, unique information may be stored and encrypted in a second database (not shown) located at an address different from an address of a location of the first database 608.

Figure 7:
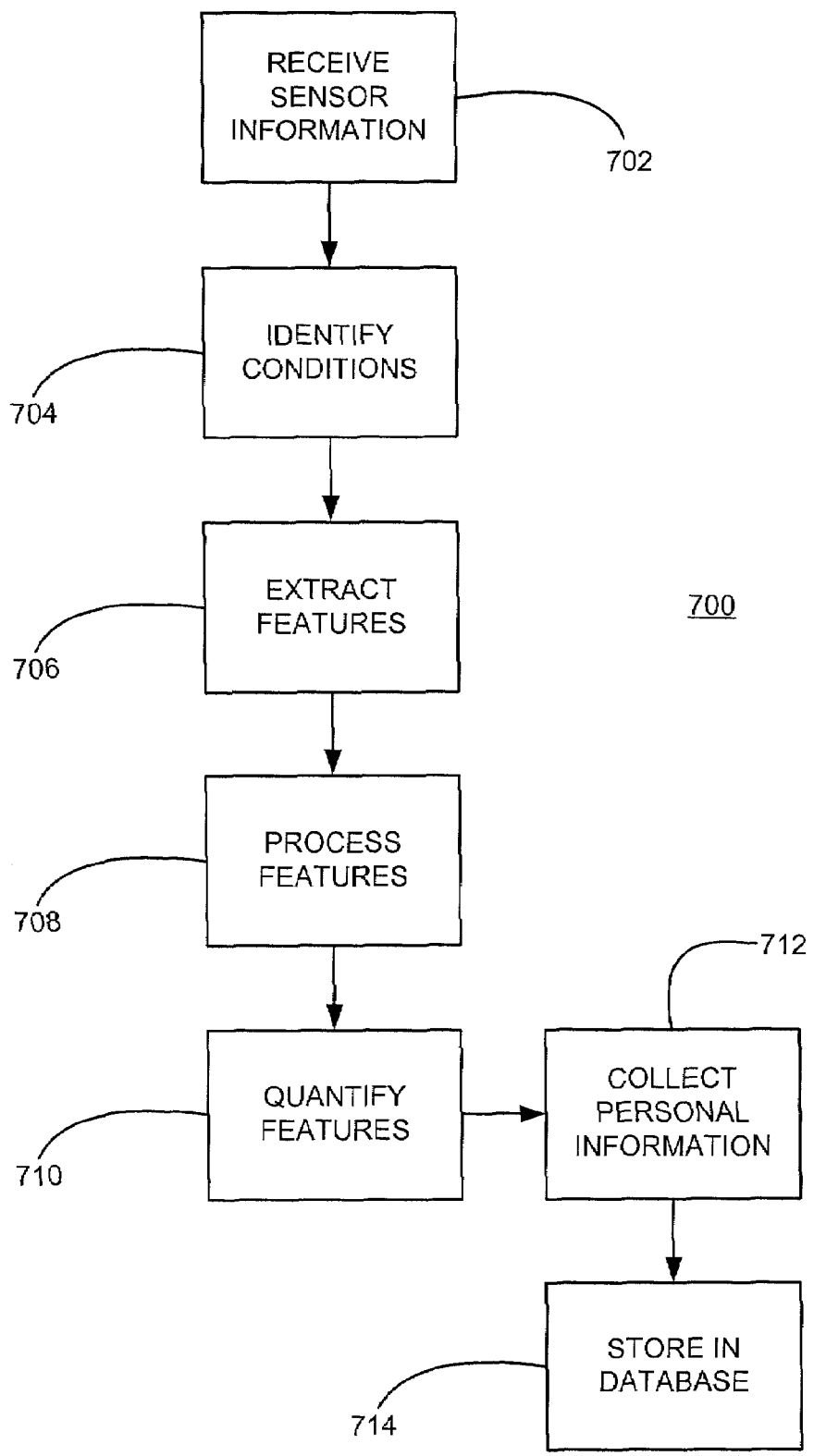
FIG. 7 illustrates an exemplary second flow chart for performing skin analysis consistent with features and principles of the present invention.
Figure 8A:
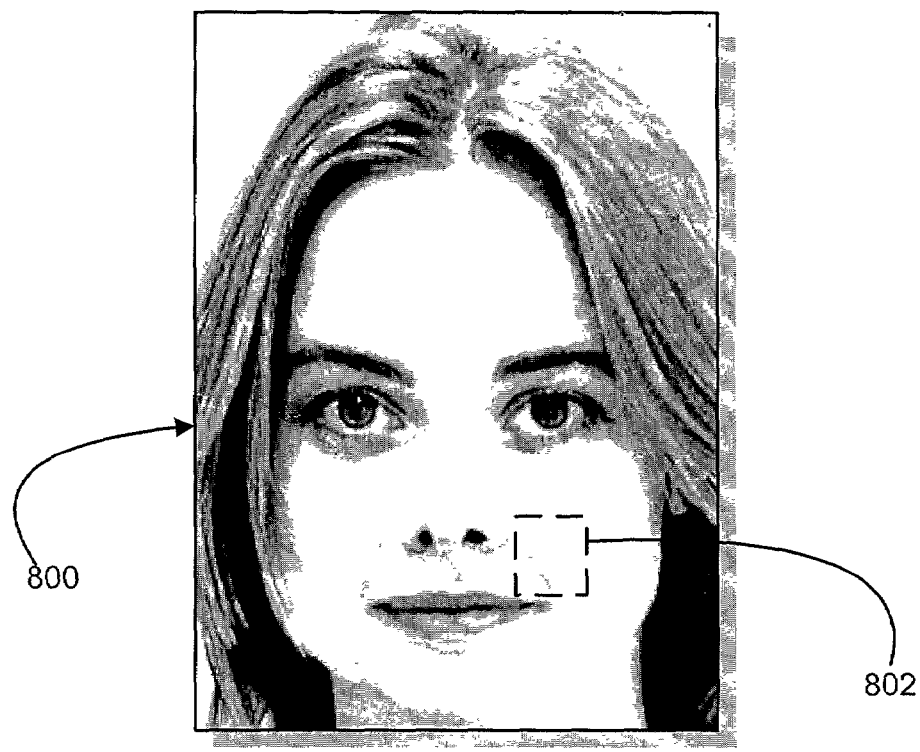
FIG. 8A illustrates an exemplary image consistent with features and principles of the present invention.
Figure 8B:
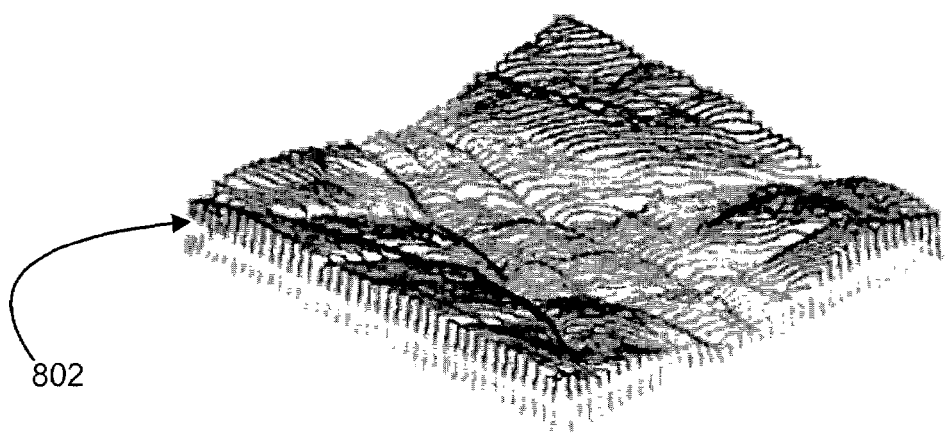
FIG. 8B illustrates an exemplary ultra-sonic topographical plot consistent with features and principles of the present invention.

Another embodiment of the invention may include a method for performing a skin analysis illustrated by a flow chart 700 in FIG. 7. In step 702 of FIG. 7, sensor information is received. Sensor information may be any information that identifies characteristics (e.g. physical, physiological, biological, and aesthetic) of a subject. As previously discussed, sensor information may be a traditional image, but the invention may use sensor information from other sources. For example, FIGS. 8A and 8B contrast an exemplary image 800 with an ultra-sonic topographical plot 802, respectively, that may be received as sensor information at step 702. The image 800 contains information on the facial skin of the subject and portions of the facial skin may have been scanned with an ultrasonic imaging device. The dotted box 802 in FIG. 8A delineates one of the portions that may be scanned. The topographical plot 802 in FIG. 8B may be a detailed surface map of the facial skin in the portion delineated by the dotted box 802.

Figure 9:
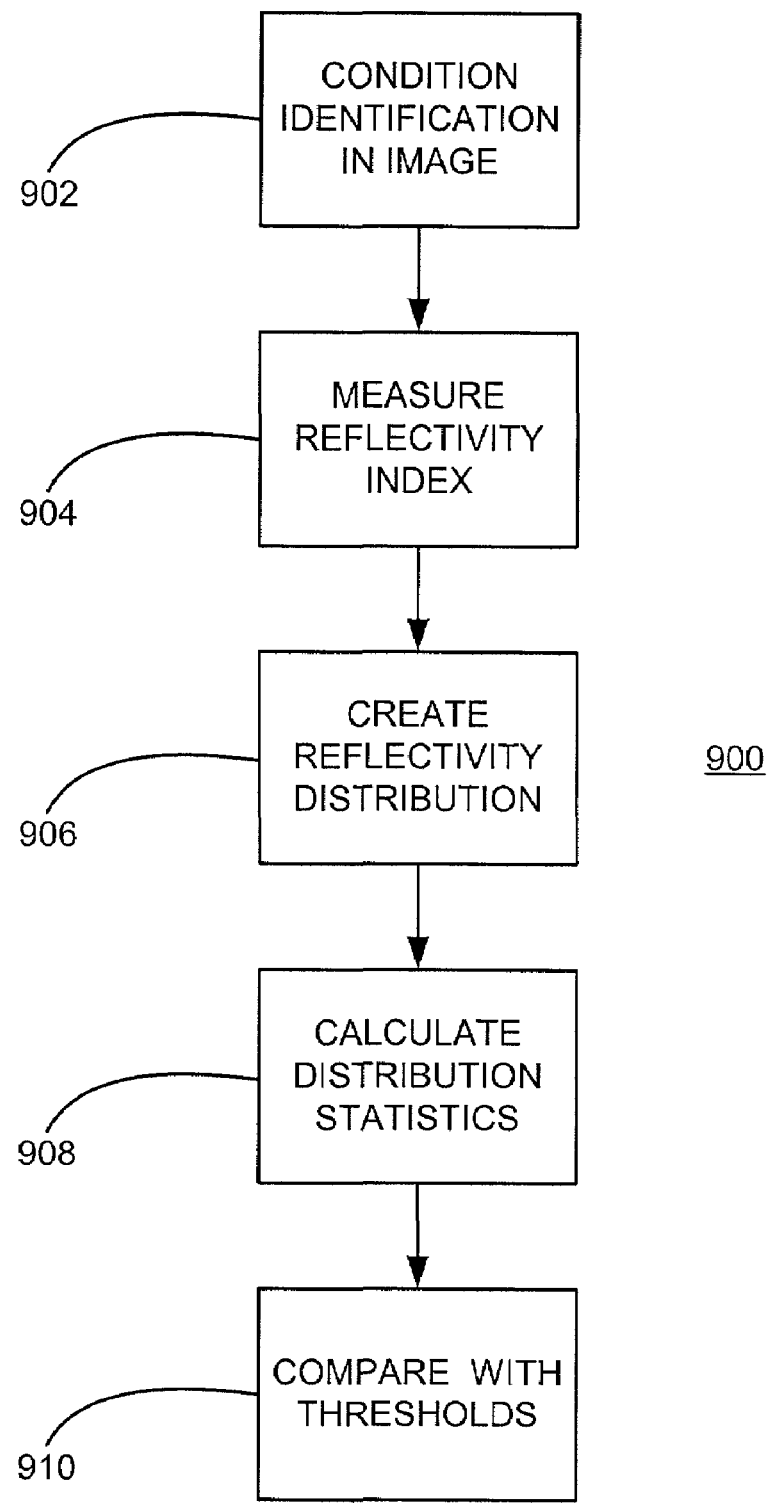
FIG. 9 illustrates an exemplary algorithm for extracting shininess features consistent with features and principles of the present invention.
Figure 10:
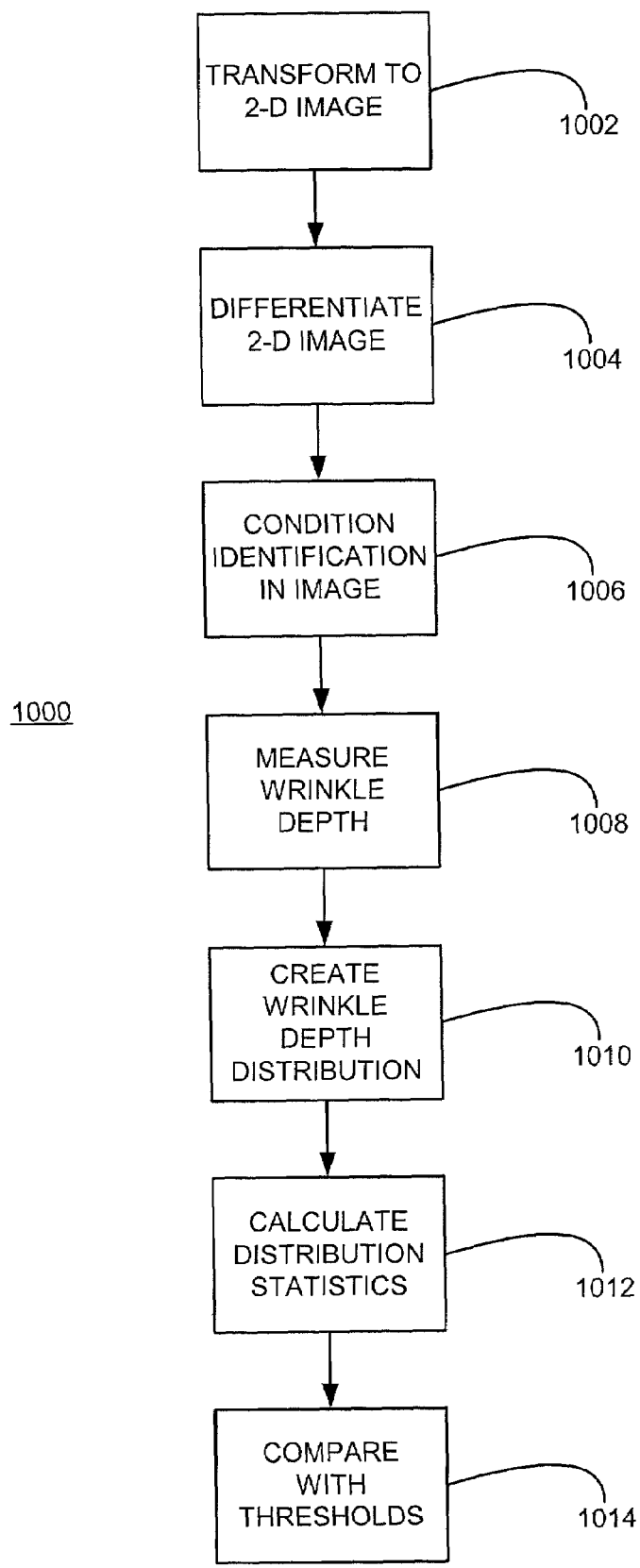
FIG. 10 illustrates an exemplary algorithm for extracting wrinkle features consistent with features and principles of the present invention.

After the sensor information is received at step 702 in FIG. 7, the subject may be requested to identify desirable and undesirable conditions in the external body condition for beauty analysis at step 704. Desirable and undesirable conditions available for beauty analysis may include skin conditions. As previously discussed, different algorithms known by persons of ordinary skill in the art and compatible with features and principles of the present invention may be used to extract features reflective of the conditions. FIGS. 9 and 10 illustrate two exemplary algorithms for extracting shininess and wrinkle features, respectively. Detailed descriptions of the exemplary algorithms are provided later herein.

Figure 11:
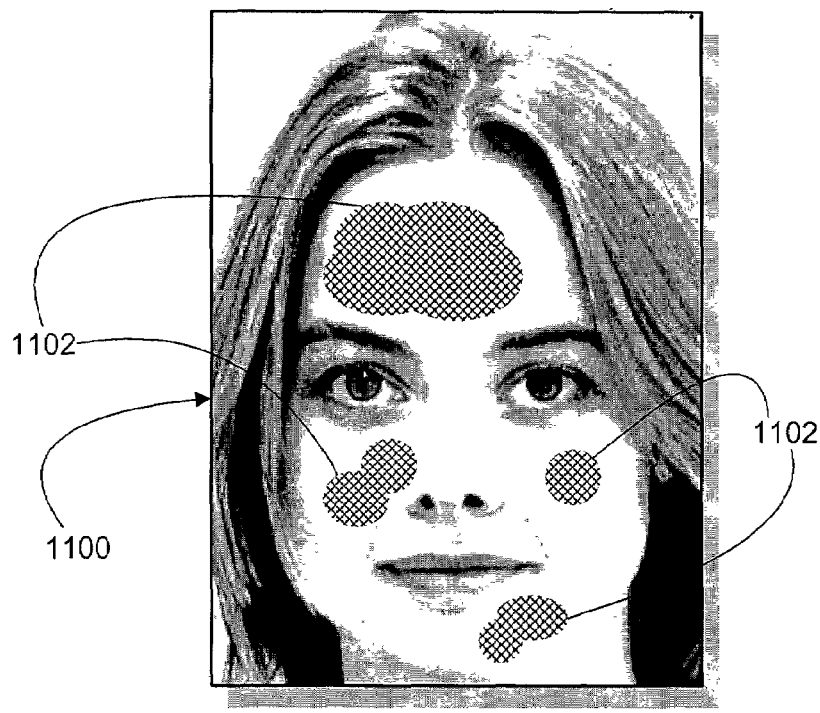
FIG. 11 illustrates an exemplary representation of reflectivity indices consistent with features and principles of the present invention.
Figure 12:
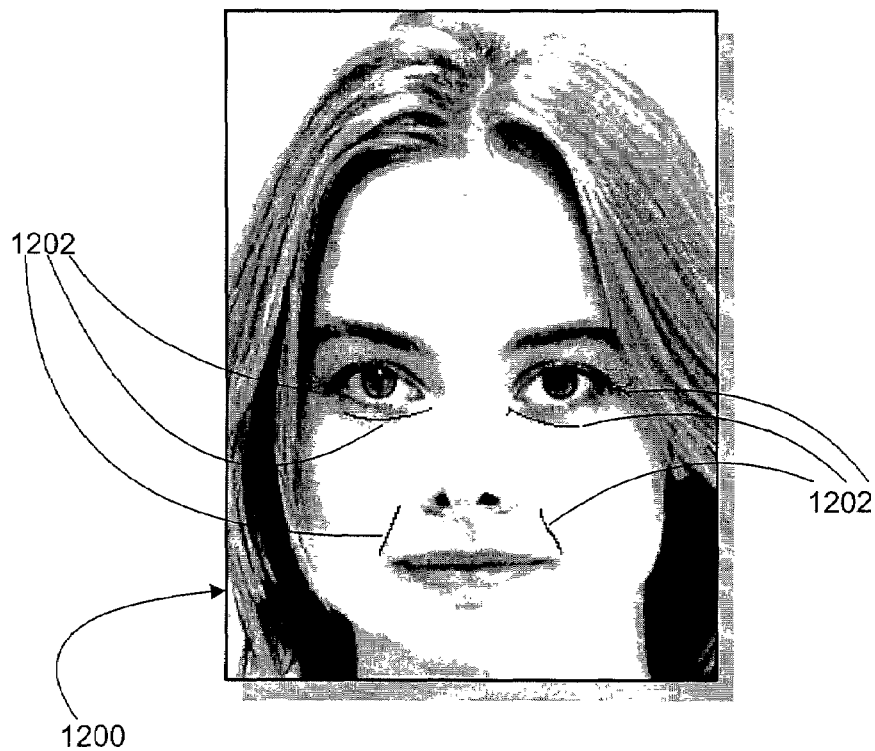
FIG. 12 illustrates an exemplary representation of substantial wrinkle depths consistent with features and principles of the present invention.

Once features are extracted at step 706 in FIG. 7, the features may be processed at step 708. Processing may include creating representations of the features and overlaying the representations of the features onto the image 800. For example, FIGS. 11 and 12 illustrate a first and a second exemplary representation of features consistent with features and principles of the present invention, respectively. In FIG. 11, a processed image 1100 contains shaded regions 1102 that mark portions of the subject's facial skin with high reflectivity indices as determined during feature extraction at step 706. Reflectivity indices are features representing the skin condition of shininess. High reflectivity indices indicate excessive shininess. In FIG. 11, a second processed image 1200 contains lines 1202 that mark portions of the subject's facial skin with substantial wrinkle depths as determined during feature extraction at step 706. Wrinkle depths are features representing the skin condition of wrinkles. Substantial wrinkle depths indicate excessive visible wrinkles. Shaded regions 1102 and lines 1202 are used above as exemplary representations of features, but any mark or visual cue, including variations of any mark or visual cue, may be used instead. Examples of variations include color, intensity, frequency, and shape of mark or visible indicator.

Figure 13:
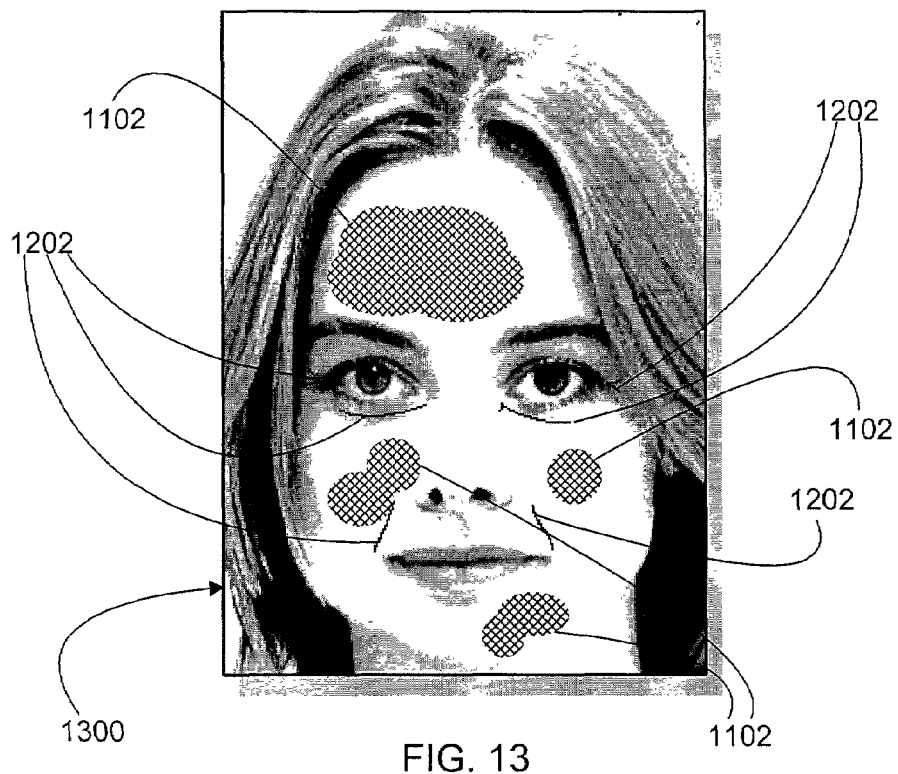
FIG. 13 illustrates an exemplary composite image consistent with features and principles of the present invention.

FIG. 13 illustrates an exemplary composite 1300 of representations of features that may be generated during features processing at step 708, consistent with features and principles of the present invention. Both representations of the high reflectivity indices and substantial wrinkle depths 1102 and 1202 are overlaid onto the image 800.

After feature processing at step 708 in FIG. 7, the feature may be quantified at step 710. Quantification of features may involve generation of metrics for desirable and undesirable conditions in the subject's external body condition. Examples of metrics for wrinkles may include average density, extent, intensity, frequency, type and severity (e.g., calculated from wrinkle depths and percentage area). Examples of metrics for shininess may include extent, intensity, frequency, type, and severity of shininess (e.g., calculated from reflectivity indices).

Further, quantification at step 710 may include tracking changes in metrics for desirable and undesirable conditions over time. For example, sensor information may be received at step 702 at various times for feature extraction at step 706, processing at step 708, and quantification at step 710. At the various times, metrics generated during quantification at step 710 may be compared and analyzed against metrics generated from sensor information received at step 702 from prior times. Quantification at step 710 may then include, for example, calculating change in metrics, average metrics, and standard deviation of metrics over time. Quantification at step 710 may also include comparing the subject's metrics against a database of other subject's metrics.

Personal information from the subject may be collected at step 712. Although depicted as following step 710, the order of steps is not material to the invention in its broadest sense. Personal information may include any data regarding the subject that may correlate with desirable and undesirable conditions. For example, it may be known that there is a correlation between smoking and wrinkles in the facial skin. Therefore smoking habits and patterns (e.g., frequency, quantity, and products used) may be collected. Or it may be known that certain diets affect the shininess of facial skin. Therefore, frequency, quantity, content, and nutritional quality of food consumed by the subject may be collected. Additional exemplary personal information collected may include characteristic, lifestyle, familial, vocational, environmental, and genetic information of the subject. Portions of the personal information, sensor information, features, and results from various steps in the method (steps 702-710) may be stored as subject information in the database at step 714.

Figure 14:
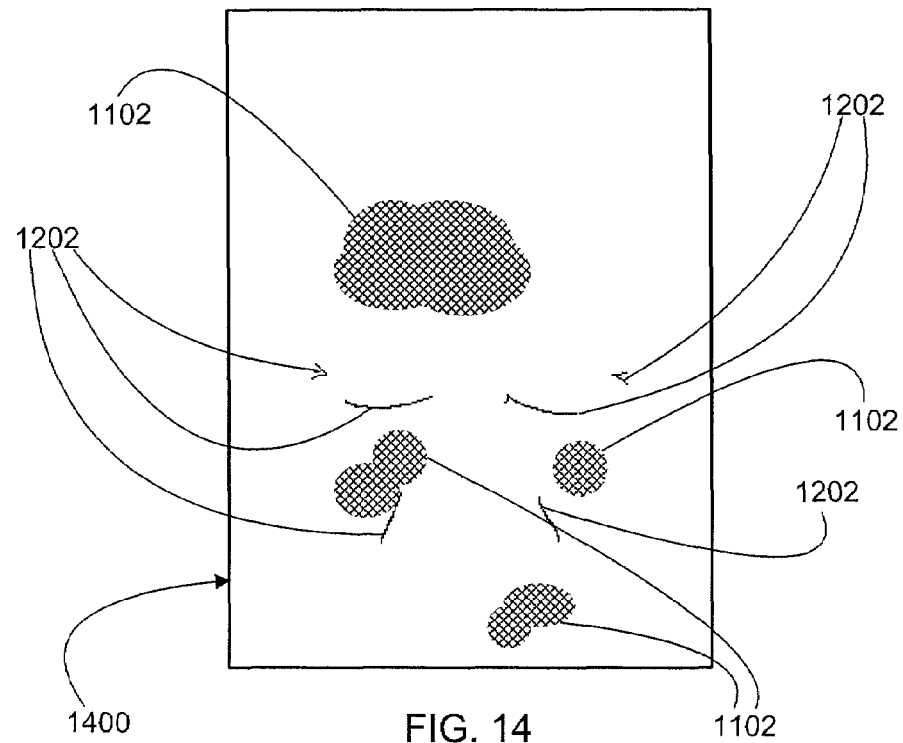
FIG. 14 illustrates an exemplary representation of features stored to a database consistent with features and principles of the present invention.

The database may contain similar subject information from other subjects. Subject information may be used to create demographical statistics. Unique information that identifies the subject (e.g., the subject name or likeness) may be excluded from the personal information or stored separately and encrypted for the purposes of privacy. Such unique information may be stored at an address location different from an address location of the database. For example, FIG. 14 illustrates an exemplary representation of features 1400 stored to a database in the method consistent with principles of the present invention. The representation of features 1400 does not include unique information identifying the subject such as the image 800 of the subject. Should the invention be used in connection with analysis of portions of the subject's body deemed by the subject to be "private", the representation may only contain information characterizing a condition of the subject, without revealing an identifiable body image.

FIG. 9 illustrates an exemplary features extraction algorithm 900 consistent with principles of the present invention. The algorithm 900 extracts reflectivity indices from the image 120. At step 902, skin conditions are identified in the image 800 using techniques known in the art. As persons of ordinary skill in the art will appreciate, an average reflectivity index is measured at step 904 for each component part also using methods know in the art.

An exemplary method for measuring the average reflectivity index at step 904 may include determining brightest and darkest component parts in a partitioned image. The brightest and darkest component parts may be assigned reflectivity indices of one and zero, respectively. Remaining component parts may be assigned reflectivity indices between one and zero based on the brightness of the remaining component parts relative to the brightest and darkest component parts. The reflectivity indices may be sorted to create a reflectivity distribution at step 906.

Figure 15:
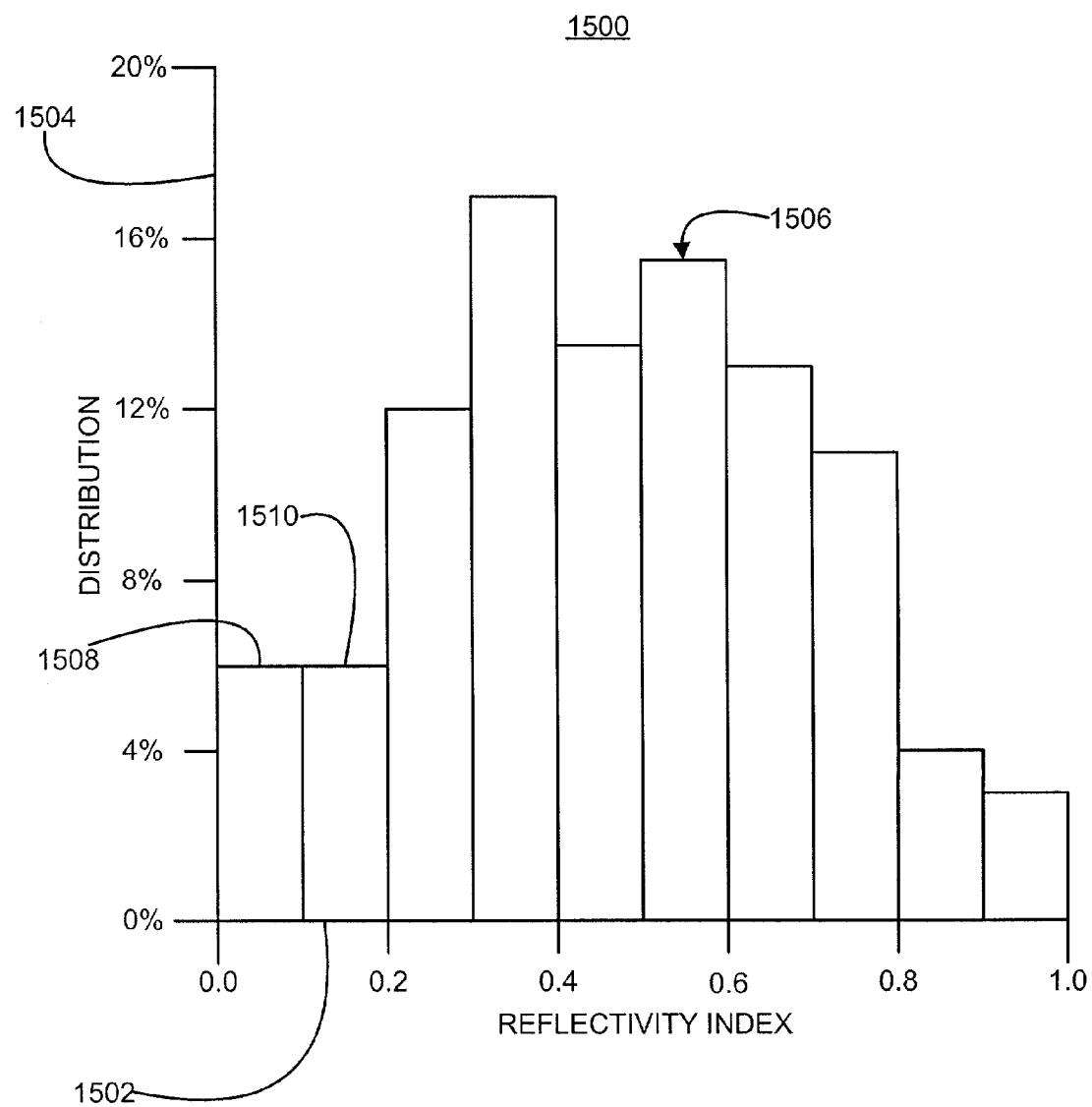
FIG. 15 illustrates an exemplary reflectivity distribution consistent with features and principles of the present invention.

FIG. 15 illustrates an exemplary reflectivity distribution 1500 consistent with features and principles of the present invention. FIG. 15 indicates percentage of component parts of an image that fall within prescribed index ranges. An abscissa axis 1502 indicates the ranges of reflectivity indices corresponding to vertical bars 1506. An ordinate axis 1504 indicates the percentage of component parts with reflectivity indices in the ranges of reflectivity indices corresponding to the vertical bars 1506. For example, a first vertical bar 1508 indicates that six percent of the component parts of the image have reflectivity indices in a range of zero to one-tenth. A second vertical bar 1510 indicates that six percent of component parts have reflectivity indices in a range of one-tenth to two-tenths.

Statistics for the reflectivity index distribution 1500 may be calculated at step 908. For example, a total average reflectivity index may be calculated to represent an average shininess of the subject's facial skin. A reflectivity standard deviation may be calculated to represent variation in shininess of the subject's facial skin. Areas in the partitioned image with excessive shininess may be determined by comparing the reflectivity indices against thresholds to cull out component parts with high reflectivity indices at step 910. For example, component parts with reflectivity indices greater than eight-tenths may be labeled. Labeling may include shading of component parts to indicate regions of excessive shininess as illustrated in FIG. 11.

FIG. 10 illustrates a second exemplary features extraction algorithm 1000 consistent with principles of the present invention. The algorithm 1000 may extract wrinkle depths from the topographical plot 802 in FIG. 8B. As a person of ordinary skill in the art of image processing will appreciate, the three-dimensional topographical plot may be transformed into a two-dimensional contour plot with an overhead perspective at step 1002 in FIG. 10. The contour plot may undergo a differential transformation that calculates slopes, referred to as derivative indices, of contours in the contour plot at step 1004. The contour plot together with the differentiated contour plot may be used to determine wrinkle depths in the subject's facial skin. By way of example, a condition may be identified in the image using the differentiated contour plot (e.g. partitioned at step 1006 into a partitioned contour plot with component parts in a manner similar to step 902 in the algorithm 900 of FIG. 9 described above). An average wrinkle depth may be measured for each component part in the partitioned contour plot at step 1008. Average wrinkle depths may be sorted to create a wrinkle depth distribution at step 1010.

Statistics for the wrinkle depth distribution may be calculated at step 1012. For example, a total average wrinkle depth may be calculated to represent an average severity of wrinkles in the subject's facial skin. A wrinkle depth standard deviation may be calculated to represent variation of wrinkles in the subject's facial skin. Areas in the partitioned contour with excessive wrinkles may be determined by comparing the wrinkle depths against thresholds to cull out component parts with substantial wrinkle depths at step 1014. Culled out component parts may be labeled. Labeling may include marking component parts to indicate regions of excessive wrinkles as illustrated in FIG. 12.

After skin conditions are identified, the invention may involve the proscription of remedies to the extent an identified condition is undesirable. For example, if the beauty analysis indicates excessive shininess or wrinkles, beauty treatments may be recommended to alleviate the excessive shininess or wrinkles. Beauty treatments for a variety of undesirable conditions may include a treatment for wrinkle reduction, anti-aging, elasticity improvement, enhance coloration, improved clarity, skin blemish removal, and freckle reduction.

Conversely, exemplary features for desirable conditions may be extracted during beauty analysis. The extraction, processing, and quantification of features for desirable conditions may be used simply as a diagnostic means without the inclusion of any beauty treatments.

This application may discuss beauty products in connection with use by women. However, it is to be understood that such discussions are for exemplary purposes only. It is to be understood that the invention is equally applicable to all genders, and is not necessarily limited to the beauty industry. It is also to be understood that any functional aspect of the invention can be implemented via any location in the system or network, and data software may be resident at any location either in a network, at a stand-alone site, or on media in the custody and control of a user or subject.

It is to be further understood that the physical mechanisms (e.g. hardware, software, networks, systems) for implementing the methods of the invention are many. Networks, hardware and systems can be configured in a host of ways with software and hardware functionality residing at many alternative locations. In addition, systems other than the exemplary systems disclosed might be used to implement the invention. Therefore, it is to be understood that the methods of the invention are not limited to any particular structure.

Further, methods or portions thereof can be implemented in either an electronic environment, a physical environment, or combinations thereof. Thus, for example, although one or more portions of a method may occur in an electronic environment, a "purchase" portion of the method may occur in a brick and mortar store, or vice versa.

Cross-reference to Concurrently Filed Applications and Global Definitions

This application claims priority on and incorporates by reference the following U.S. Provisional applications: Artificial Intelligence For Use In Cosmetic And Non-Cosmetic Environments, Application No. 60/325,561 (provisional filed Oct. 01, 2001); and Methods And Systems For Cosmetic And Non-Cosmetic Product Selection, Application No. 60/325,559 (provisional filed Oct. 1, 2001).

The following concurrently filed U.S. patent applications are also incorporated herein by reference: Body Image Enhancement, U.S. patent application Ser. No. 10/024,480; Methods And Systems For Predicting And/Or Tracking Changes In External Body Conditions, U.S. patent application Ser. No. 10/024,354; Methods And Systems For Generating A Prognosis, U.S. patent application Ser. No. 10/024,333; Historical Beauty Record, U.S. patent application Ser. No. 10/024,622; Identification And Presentation Of Analogous Beauty Case Histories, U.S. patent application Ser. No. 10/024,332; Interactive Beauty Analysis, U.S. patent application Ser. No. 10/024,481; Simulation Of An Aesthetic Feature On A Facial Image, U.S. patent application Ser. No. 10/024,353; Beauty Advisory System And Method, U.S. patent application Ser. No. 10/024,496; Virtual Beauty Consultant, U.S. patent application Ser. No. 10/024,620; Calibrating Image Capturing, U.S. patent application Ser. No. 10/024,334; Use Of Artificial Intelligence In Providing Beauty Advice, U.S. patent application Ser. No. 10/024,616; Shop-In-Shop Website Construction, U.S. patent application Ser. No. 10/024,352; Early Detection Of Beauty Treatment Progress, U.S. patent application Ser. No. 10/024,619; Cosmetic Affinity Indexing, U.S. patent application Ser. No. 10/024,356; Systems And Methods For Providing Beauty Guidance, U.S. patent application Ser. No. 10/024,621; Methods And Systems Involving Simulated Application Of Beauty Products, U.S. patent application Ser. No. 10/024,355; Customized Beauty Tracking Kit, U.S. patent application Ser. No. 10/024,351; Analysis Using Three-Dimensional Facial Image U.S. patent application Ser. No. 10/024,615; Body Image Templates With Pre-Applied Beauty Products, U.S. patent application Ser. No. 10/024,482; and Image Capture Method, U.S. patent application Ser. No. 10/024,651.

To the extent not inconsistent with the invention defined herein, definitions and terminology usage in the above-mentioned concurrently filed applications, the above-mentioned priority applications, and the following global definitions are to be considered in interpreting the language of this patent and the claims herein. Where multiple definitions are provided, they should be considered as a single cumulative definition.

The term "image" may include one or more of two-dimensional and three-dimensional representations. In certain examples consistent with the invention, a plurality of images from different perspectives may be used to construct a three-dimensional image. In a broader sense, only a single image may be used. Depending on the embodiment, the term "image" may include either a visually perceptible image or electronic image data that may be either used to construct a visually perceptible image or to derive information about the subject. The image may be a body image corresponding to an anatomical portion of the subject, and may represent, for example, the subject's entire face, or a portion of the subject's face. The image may be a detailed picture (e.g., a digital image or a photograph) of a portion of the subject's body and/or a topological plot mapping contours of a portion of subject's body. If the image is representative of an external body condition, the image could be either an actual image showing the condition or an image including symbolizations of the condition, for example. The image may be an actual or a simulated image. Simulated images may include wholly or partially generated computer images, images based on existing images, and images based on stored features of a subject.

The term "image capture device", similar terms, and terms representing structures with similar functions may include one or more of a digital camera, webcam, film camera, analog camera, digital video camera, scanner, facsimile machine, copy machine, infrared imager, ultra-sound imaging device, or any other mechanism for acquiring an image of a subject's external body condition, an image of the subject's countenance, an/or an image of the subject's skin. An ultrasonic device might provide skin thickness information, or it might create a map on an area of the external location. Thus, the term "image" as used herein may be broader than a picture. Combinations of image capture devices may be used. For example, an image captured on photographic paper using a film camera might then be scanned on a flat bed scanner to create another image.

The term "capturing (an image)", or any form thereof, refers to the use of an image capture device to acquire an image. "Capturing" may refer to the direct act of using the image capture device to acquire the image. It may also include indirect acts to promote acquisition. To this end, "capturing" may include the indirect acts of providing access to hardware, or to at least one of a client-based algorithm and a server-based algorithm for causing the image capture device to capture an image. This may be accomplished by providing a user with software to aid in the image capture process, or providing the user with access to a network location at which the software resides. Also consistent with certain embodiments of the invention, capturing may include at least one of receiving an instruction from the subject to capture an image, indicating to the subject before the image is captured, and indicating to the subject when the image is captured.

The term "image processing technique" or similar terms, may include a software program, computer, application specific integrated circuit, electronic device and/or a processor designed to identify in an image one or more characteristics, such as a skin condition. Such techniques may involve binarization, image partitioning, Fourier transforms, fast Fourier transforms (FFTs), and/or discrete cosine transforms may be performed on all or part of the image, resulting in coefficients. Based on the coefficients, conditions may be located, as known in the art. Artificial intelligence, such as fuzzy logic, neural networks, genetic programming and decision tree programming, may also be used to identify conditions. Alternatively, one or more digital filters may be passed through the image for locating specific conditions. These examples are provided for illustrative purposes with the understanding that any image processing technique may be used.

The term "network interface" or similar terms, refer to any mechanism for aiding communications between various nodes or locations in a network. A network interface may include, for example a bus, a modem, or any other input/output structure. A network interface may permit a connection to any network capable of being connected to an input and/or output module located within at least one or more of the following exemplary networks: an Ethernet network, an Internet Protocol network, a telephone network, a radio network, a cellular network, or any mechanism for permitting communication between two or more modes or remote locations. In some invention embodiments, a network interface might also included a user interface.

The term "user interface" may include at least one component such as a keyboard, key pad, mouse, track ball, telephone, scanner, microphone, touch screen, web cam, interactive voice response system (IVR), voice recognition system or any other suitable input mechanism for conveying information. A user interface may also include an input port connected by a wired, optical, or wireless connection for electromagnetic transmissions. In some embodiments, a user interface may include connections to other computer systems to receive the input commands and data therefrom. User interface may further include a data reading device such as a disk drive for receiving input data from and writing data to storage media such as magnetic and optical disks.

As used herein terms such as "external body condition", "skin condition", and "actual condition" refer to conditions of at least one of the skin, teeth, hair, eyebrows, eyelashes, body hair, facial hair, fingernails, and/or toenails, or any other externality. Examples of skin conditions may include elasticity, dryness, cellulitis, sweating, aging, wrinkles, melanoma, exfoliation, desquamation, homogeneity of color, creases, liver spots, clarity, lines, micro-circulation, shininess, softness, smoothness, tone, texture, matitty, hydration, sag, suppleness, stress, springiness, firmness, sebum production, cleanliness, translucency, luminosity, irritation, redness, vasocolation, vasomotion, vasodilation, vasoconstriction, pigmentation, freckles, blemishes, oiliness, pore distribution, pore size, moles, birthmarks, acne, blackheads, whiteheads, pockmarks, warts, pustules, boils, blisters, marks, smudges, specks, psoriasis and other characteristics associated with the subject's skin. Examples of hair conditions may include keratin plug, length, dryness, oiliness, dandruff, pigmentation, thickness, density, root conditions, split ends, hair loss, hair thinning, scales, staging, cleanliness and other properties related to the subject's hair. Examples of fingernail and toenail conditions may include onychomycosis, split nails, delaminating, psoriasis, brilliancy, lines, spots, coloration, gloss, strength, brittleness, thickness, hangnail, length, disease, and other characteristics related to the subject's nails. Other conditions may include, for example, size and proportion of facial features, teeth discoloration, and any other aesthetic-related or physical, physiological, or biological conditions of the user.

"Enabling", "facilitating", and "causing" an action refer to one or more of a direct act of performing the action, and any indirect act of encouraging or being an accessory to the action. Thus, the terms include partnering or cooperating with an entity who performs the action and/or referring commerce to or having commerce referred from an entity who performs the action. Other examples of indirect activity encompassed within the definitions of "enabling", "facilitating", and "causing" may include providing a subject with one or more of tools to knowingly aid in performing the action, providing instructions on how to perform the action, providing prompts or cues to perform the action, or expressly encouraging performance of the action. Indirect activity may also include cooperating with an entity who either directly performs the action or who helps another perform the action. Tools may include software, hardware, or access (either directly, through hyperlink, or some other type of cooperation or partnering) to a network location (e.g., web site) providing tools to aid in performing the action. Thus, phrases such as "enabling access" and "enabling display" do not necessary require that the actor actually access or display anything. For example, the actor may perform the enabling function by affiliating with an entity who performs the action, or by providing instructions, tools, or encouragement for another to do the accessing and displaying.

Forms of the word "displaying" and like terms may also include indirect acts such as providing content for transmission over a network to a display device, regardless of whether the display device is in the custody or control of the sender. Any entity in a chain of delivering information for display performs an act of "displaying", as the term is used herein.

Likewise, the term "providing" includes direct and indirect activities. For example, providing access to a computer program may include at least one of providing access over a network to the computer program, and creating or distributing to the subject a computer program configured to run on the subject's workstation or computer. For example, a first party may direct network traffic to (either through electronic links or through encouragement to visit) a server or web site run by a second party. If the second party maintains a particular piece of software thereon, then it is to be understood that within the meaning of "providing access" as used herein, the first party is said to provide access to the particular software. Or if the first party directs a subject to a second party who in turn ships the particular software to the user, the first party is said to provide the user with access to the particular software. (Of course, in both of the above instances, the second party would also be providing access within the meaning of the phrase as used herein.) "Receiving" may include at least one of acquisition via a network, via verbally communication, via electronic transmission, via telephone transmission, in hard-copy form, or through any other mechanism enabling reception. In addition, "receiving" may occur either directly or indirectly. For example, receipt may occur through a third party acting on another party's behalf, as an agent of another, or in concert with another. Regardless, all such indirect and direct actions are intended to be covered by the term "receiving" as used herein. A received request, for example, may take one of many forms. It may simply be a checked box, clicked button, submitted form or oral affirmation. Or it might be a typed or handwritten textual request. Receiving may occur through an on-line interest form, e-mail, facsimile, telephone, interactive voice response system, or file transfer protocol transmitted electronically over a network at a web site, an internet protocol address, or a network account. A request may be received from a subject for whom information is sought, or an entity acting on the subject's behalf. "Receiving" may involve receipt directly or indirectly through one or more networks and/or storage mediums. Receipt may occur physically such as in hard copy form, via mail delivery or other courier delivery.

Forms of the word "maintain" are used broadly to include gathering, storing, accessing, providing access to, or making something available for access, either directly or indirectly. For example, those who maintain information include entities who provide a link to a site of a third party where the information is stored.

Consistent with the concepts set forth above, all other recited actions such as, for example, obtaining, determining, generating, selecting, applying, simulating, presenting, etc, are inclusive of direct and indirect actions. Thus, for purposes of interpreting the following claims, an entity performs a recited action through either direct or indirect activity. Further examples of indirect activity include sending signals, providing software, providing instructions, cooperating with an entity to have the entity perform the action, outsourcing direct or indirect actions, or serving in any way as an accessory to the specified action.

The term "product" is used to generically refer to tangible merchandise, goods, services, and actions performed. A "beauty product," "beauty care product," "cosmetic product" or similar terms, refer to products (as defined above) for effecting one or more external body conditions, such as conditions of the skin, hair and nails. Examples of tangible merchandise forms of beauty products include cosmetic goods, such as treatment products, personal cleansing products, and makeup products, in any form (e.g., ointments, creams, gels, sprays, supplement, ingesta, inhalants, lotions, cakes, liquids, and powders.)

Examples of services forms of beauty products include hair styling, hair cutting, hair coloring, hair removal, skin treatment, make-up application, and any other offering for aesthetic enhancement. Examples of other actions performed include massages, facial rubs, deep cleansings, applications of beauty product, exercise, therapy, or any other action effecting the external body condition whether performed by a professional, the subject, or an acquaintance of the subject.

The following is exemplary and non-exhaustive listing of a few beauty products-scrubs, rinses, washes, moisturizers, wrinkle removers, exfoliates, toners, cleansers, conditioners, shampoos, cuticle creams, oils, and anti-fungal substances, anti-aging products, anti-wrinkle products, anti-freckle products, skin conditioners, skin toners, skin coloring agents, tanners, bronzers, skin lighteners, hair coloring, hair cleansing, hair styling, elasticity enhancing products, agents, blushes, mascaras, eyeliners, lip liners, lipsticks, lip glosses, eyebrow liners, eye shadows, nail polishes, foundations, concealers, dental whitening products, cellulite reduction products, hair straighteners and curlers, and weight reduction products. A beauty care treatment regimen may involve the administration of one or more products, as defined above.

The terms "beauty advice", "beauty guidance", and similar terms are used interchangeably to refer to the provision of beauty related information to a subject. Advice or guidance includes one or more of beauty product recommendations (e.g., cosmetic product recommendations for products to treat conditions the subject is prompted to evaluate), remedial measures, preventative measures, predictions, prognoses, price and availability information, application and use information, suggestions for complementary products, lifestyle or dietary recommendations, or any other information intended to aid a subject in a course of future conduct, to aid a subject in understanding past occurrences, to reflect information about some future occurrences related to the subject's beauty or to aid a subject in understanding beauty products, as defined above.

The term "network" may include a public network such as the Internet or a telephony network, a private network, a virtual private network, or any other mechanism for enabling communication between two or more nodes or locations. The network may include one or more of wired and wireless connections. Wireless communications may include radio transmission via the airwaves, however, those of ordinary skill in the art will appreciate that various other communication techniques can be used to provide wireless transmission including infrared line of sight, cellular, microwave, satellite, blue-tooth packet radio and spread spectrum radio. Wireless data may include, but is not limited to, paging, text messaging, e-mail, Internet access and other specialized data applications specifically excluding or including voice transmission.

In some instances consistent with the invention, a network may include a courier network (e.g. postal service, United Parcel Service, Federal Express, etc.). Other types of networks that are to be considered within the scope of the invention include local area networks, metropolitan area networks, wide area networks, ad hoc networks, or any mechanism for facilitating communication between two nodes or remote locations.

"Artificial intelligence" (AI) is used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, or soft computing. Employing any computationally intelligent techniques, the AI engine may learn to adapt to unknown or changing environment for better performance. AI engines may be implemented or provided with a wide variety of components or systems, including one or more of the following: central processing units, co-processors, memories, registers, or other data processing devices and subsystems.

AI engines may be trained based on input such as product information, expert advice, user profile, or data based on sensory perceptions. Using input an AI engine may implement an iterative training process. Training may be based on a wide variety of learning rules or training algorithms. For example, the learning rules may include one or more of the following: back-propagation, real-time recurrent learning, pattern-by-pattern learning, supervised learning, interpolation, weighted sum, reinforced learning, temporal difference learning, unsupervised learning, or recording learning. As a result of the training, AI engine may learn to modify its behavior in response to its environment, and obtain knowledge. Knowledge may represent any information upon which AI engine may determine an appropriate response to new data or situations. Knowledge may represent, for example, relationship information between two or more products. Knowledge may be stored in any form at any convenient location, such as a database.

Since AI engine may learn to modify its behavior, information describing relationships for a universe of all combinations of products may not need to be maintained by the AI engine or any other component of the system.

"Personal information", "subject specific information", "user specific information", "user profile", "personal characteristics", "personal attributes", "profile information", and like terms (collectively referred to in this section as "personal information") may broadly encompass any information about the subject or user. Such information may, for example, fall within categories such as physical characteristics, fashion preferences, demographics, nutritional information, cosmetic usage information, medical history information, environmental information, beauty product usage information, lifestyle, and may include information such as name; age; birth date; height; weight; ethnicity; eating habits; vacation patterns; geographic location of the individual's residence, location, or work; work habits; sleep habits; toiletries used; exercise habits; relaxation habits; beauty care habits; smoking and drinking habits; sun exposure habits; use of sunscreen; propensity to tan; number of sunburns and serious sunburns; dietary restrictions; dietary supplements or vitamins used; diagnosed conditions affecting the external body, such as melanoma; an image, such as a picture or a multimedia file of the subject; facial feature characteristics; family history information such as physical characteristics information about relatives of the subject (e.g., premature balding, graying, wrinkles, etc.); external body condition (as defined previously); color preferences, clothing style preferences, travel habits; entertainment preferences; fitness information; adverse reactions to products, compounds, or elements (e.g., sun exposure); body chemistry, use of prior beauty care products and their effectiveness; purchasing, shopping, and browsing habits; hobbies; marital status; whether the subject is a parent; country of residence; region of residence; birth country and region; religious affiliation; political affiliation; whether the subject is an urban dweller suburban dweller or rural area dweller; size of urban area in which the subject lives; whether the subject is retired; annual income, sexual preference, or any other information reflecting habits, preferences, or affiliations of the subject.

Personal information may also include information electronically gleaned by tracking the subject's electronic browsing or purchasing habits, or as the result of cookies maintained on the subject's computer, responses to surveys, or any other mechanism providing information related to the subject. In addition, personal information may be gathered through non-electronic mechanisms such as hard copy surveys, personal interviews, or consumer preference polls.

"Complementary" and "complementary product" refers to one or more of physical, physiological, biologically, and aesthetic compatibility. A product may be complementary with one or more of another product, a group of products, or a subject. In that latter instance, whether a product is considered "complementary" may be a function of personal information of the subject. Thus, for example a product may be complementary if it is unlikely to cause an adverse allergic reaction; if it physically blends well with another product; or if it is aesthetically consistent with the subject or one or more other products. Aesthetic compatibly may refer to the fact that two products are aesthetically appealing (or do not clash) when worn together. The identification of a complementary product may also be based on product characteristics, user preferences, survey data, or expert advice.

As used herein, the words "may" and "may be" are to be interpreted in an open-ended, non-restrictive manner. At minimum, "may" and "may be" are to be interpreted as definitively including structure or acts recited. Further, the word "or" is to be interpreted in the conjunctive and the disjunctive.

While flow charts presented herein illustrate a series of sequential blocks for exemplary purposes, the order of blocks is not critical to the invention in its broadest sense. Further, blocks may be omitted and others added without departing from the spirit of the invention. Also, the invention may include combinations of features described in connection with differing embodiments.

Although a focus of the disclosure may be on server-side methods, it is nevertheless to be understood that the invention includes corresponding client-side methods, software, articles of manufacture, and computer readable media, and that computer readable media can be used to store instructions for some or all of the methods described herein. Further, it is to be understood that disclosed structures define means for implementing the functionality described herein, and that the invention includes such means for performing the disclosed functions.

In the foregoing Description of Exemplary Embodiments, various features are grouped together in a single embodiment for purposes of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Description of the Exemplary Embodiments, with each claim standing on its own as a separate embodiment of the invention.

What is claimed is:

1. A method of performing a skin analysis and maintaining a subject's privacy, the method comprising:
   receiving at least one image of at least one portion of a subject's facial skin, wherein the at least one image includes facial features enabling substantial identification of the subject's identity;
   identifying in the at least one image at least one skin condition, wherein during identifying, the at least one image is processed to identify substantially all visible occurrences of the at least one skin condition in at least one part of the at least one image;
   extracting from the at least one image at least one representation of the at least one skin condition, wherein the extracted representation includes a skin condition image devoid of substantially all facial features other than the at least one skin condition;
   storing information reflective of the at least one representation; and
   displaying the skin condition image such that the subject is substantially unidentifiable.

2. The method of claim 1, wherein the stored information includes an image of the at least one skin condition.

3. The method of claim 1, wherein the stored information includes a quantification of the at least one representation.

4. The method of claim 3, wherein the quantification indicates at least one of an extent, intensity, frequency, type, and severity of the at least one skin condition.

5. The method of claim 1, wherein the at least one skin condition includes at least one wrinkle.

6. A method of performing a skin analysis and maintaining a subject's privacy, the method comprising:
   receiving at least one image of at least one portion of a subject's facial skin, wherein the at least one image includes facial features enabling substantial identification of the subject's identity;
   identifying at least one skin condition in the at least one image of the at least one portion of the subject's facial skin, the at least one skin condition including at least one wrinkle,
   wherein during identifying, the at least one image of the at least one portion of the subject's facial skin is processed to identify substantially all visible wrinkles in at least one part of the at least one image of the at least one portion of the subject's facial skin;
   extracting at least one representation of the at least one skin condition from the at least one image of the at least one portion of the subject's facial skin, wherein the at least one extracted representation includes a skin condition image devoid of substantially all facial features other than the visible wrinkles; and
   displaying the skin condition image such that the subject is substantially unidentifiable.

7. The method of claim 6, wherein the visible wrinkles are represented in the extracted representation by marks mirroring contours and locations of the visible wrinkles.

8. The method of claim 7, wherein wrinkle depth is reflected in the extracted representation by at least one of mark intensity, color, and visual cue.

9. The method of claim 1, wherein during receiving, the at least one image is obtained in digital form.

10. The method of claim 1, wherein during identifying, a computer processor is used to perform an image processing function.

11. The method of claim 1, wherein the at least one skin condition includes at least one of skin pore size, texture, elasticity, dryness, cellulitis, sweating, aging, wrinkles, melanoma, exfoliation, desquamation, homogeneity of color, micro-circulation, shininess, softness, smoothness, hydration, sebum production, cleanliness, irritation, redness, vasomotion, vasodilation, vasoconstriction, pigmentation and freckles.

12. The method of claim 1, wherein storing includes saving the at least one representation at a geographical address separate from a geographical address of the at least one image.

13. The method of claim 1, further comprising instructing the subject on how to record the at least one image.

14. The method of claim 13, wherein instructing includes advising the subject on how to capture the at least one image with an image capture device.

15. The method of claim 14, wherein the image capture device is a digital camera.

16. The method of claim 13, wherein instructing includes advising the subject on how to capture the at least one image using a scanner.

17. The method of claim 1, further comprising associating personal information about the subject with the information reflective of the at least one representation.

18. The method of claim 17, wherein the personal information includes at least one of physical characteristics, lifestyle information, family history information, vocational information, environmental information, genetic information, and information correlated to the at least one skin condition.

19. The method of claim 18, performed on a plurality of subjects, the method further comprising maintaining a searchable database for correlating personal information of the plurality of subjects with skin conditions of the plurality of subjects.

20. The method of claim 3, wherein the quantification is tracked over time.

21. A method of performing a skin analysis and maintaining a subject's privacy, the method comprising:
receiving at least one image of at least one portion of a subject's facial skin, wherein the at least one image includes facial features enabling substantial identification of the subject's identity;
identifying at least one skin condition in the at least one image of the at least one portion of the subject's facial skin;
extracting at least one representation of the at least one skin condition from the at least one image of the at least one portion of the subject's facial skin,
wherein extracting occurs to an extent that the subject is anonymous when the representation is viewed; and
displaying the representation such that the subject is anonymous.

22. The method of claim 1, wherein during extracting at least one portion of the at least one image is magnified to facilitate identifying the at least one skin condition.

23. A method of performing a skin analysis, the method comprising:
receiving at least one image of at least one portion of a subject's facial skin, wherein the at least one image includes facial features enabling substantial identification of the subject's identity;
identifying in the at least one image at least one skin condition;
extracting from the at least one image at least one representation of the at least one skin condition, wherein the extracted representation includes a skin condition image devoid of substantially all facial features other than the at least one skin condition; and
storing information reflective of the at least one representation,
wherein skin in the received image is covered with powder to facilitate extracting the at least one representation.

24. A method of performing a skin analysis, the method comprising:
receiving at least one image of at least one portion of a subject's facial skin, wherein the at least one image includes facial features enabling substantial identification of the subject's identity;
identifying in the at least one image at least one skin condition;
extracting from the at least one image at least one representation of the at least one skin condition, wherein the extracted representation includes a skin condition image devoid of substantially all facial features other than the at least one skin condition; and
storing information reflective of the at least one representation,
wherein skin in the received image is illuminated with a Woods lamp to facilitate extracting the at least one representation.

25. The method of claim 1 conducted, at least in part, in a network environment, wherein receiving at least one image occurs via a network and in at least one location remote from a location of the subject.

26. A method of performing a skin analysis and maintaining a subject's privacy, the method comprising:
receiving an image of a portion of a subject's skin, wherein the image includes facial features enabling substantial identification of the subject's identity;
identifying in the image at least one skin condition, wherein during identifying, the at least one image is processed to identify substantially all visible occurrences of the at least one skin condition in at least one part of the at least one image;
extracting from the image at least one representation of the at least one skin condition, wherein the extracted representation includes a skin condition image devoid of substantially all facial features other than the at least one skin condition;
storing information reflective of the at least one representation; and
displaying the skin condition image such that the subject is substantially unidentifiable.

27. The method of claim 26, wherein during extracting at least a portion of the at least one image is magnified to facilitate identifying the at least one skin condition.

28. A method of performing a skin analysis, the method comprising:
receiving an image of a portion of a subject's skin, wherein the subject is substantially identifiable in the at least one image;
identifying in the image at least one skin condition;
extracting from the image at least one representation of the at least one skin condition, wherein the extracted representation includes a skin condition image devoid of substantially all features that identify the subject; and
storing information reflective of the at least one representation,
wherein skin in the received image is covered with powder to facilitate extracting the at least one representation.

29. A method of performing a skin analysis, the method comprising:
receiving an image of a portion of a subject's skin, wherein the subject is substantially identifiable in the at least one image;
identifying in the image at least one skin condition;
extracting from the image at least one representation of the at least one skin condition, wherein the extracted representation includes a skin condition image devoid of substantially all features that identify the subject; and
storing information reflective of the at least one representation,
wherein skin in the received image is illuminated with a Woods lamp to facilitate extracting the at least one representation.

30. The method of claim 26 conducted, at least in part, in a network environment, wherein receiving an image occurs via a network and in at least one location remote from a location of the subject.

31. A system for performing a skin analysis and maintaining a subject's privacy, the system comprising:
- first memory for storing an image of at least a portion of a subject's facial skin, wherein the image includes facial features enabling substantial identification of the subject's identity;
- processor configured to identify in the image at least one skin condition and for extracting from the image at least one representation of the at least one skin condition to thereby protect the subject's identity; and
- second memory for storing information reflective of the at least one representation.

32. A method of protecting an identity of an individual providing a body image, the method comprising:
- instructing the subject to capture at least one image of at least one portion of the subject, the image containing information for use in a skin analysis and information unrelated to a skin analysis, including facial features enabling substantial identification of the subject's identity;
- providing software for modifying the at least one image to remove at least some of the information unrelated to the skin analysis, thereby protecting the subject's identity during transmission;
- receiving the modified image over a network; and
- performing a skin analysis on the modified image.

33. A method of performing a hair analysis, the method comprising:
- receiving at least one image of at least one portion of a subject's hair;
- identifying in the at least one image at least one hair condition;
- extracting from the at least one image at least one representation of the at least one hair condition; and
- storing information reflective of the at least one representation.

34. The method of claim 33 conducted, at least in part, in a network environment, wherein receiving at least one image occurs via a network and in at least one location remote from a location of the subject.

35. A method of performing a nail analysis, the method comprising:
- receiving at least one image of at least one portion of a subject's nails;
- identifying in the at least one image at least one nail condition;
- extracting from the at least one image at least one representation of the at least one nail condition; and
- storing information reflective of the at least one representation.

36. The method of claim 35 conducted, at least in part, in a network environment, wherein receiving at least one image occurs via a network and in at least one location remote from a location of the subject.

* * * * *

UNITED STATES PATENT AND TRADEMARK OFFICE
CERTIFICATE OF CORRECTION

| | | |
|---|---|---|
| PATENT NO. | : 7,324,668 B2 | Page 1 of 1 |
| APPLICATION NO. | : 10/024495 | |
| DATED | : January 29, 2008 | |
| INVENTOR(S) | : Gilles Rubinstenn et al. | |

It is certified that error appears in the above-identified patent and that said Letters Patent is hereby corrected as shown below:

In claim 21, column 19, line 22, "subiect's" should read --subject's--.

In claim 29, column 20, line 57, "subiect;" should read --subject;--.

In claim 31, column 21, line 6, "subiect's" should read --subject's--.

Signed and Sealed this

Tenth Day of June, 2008

JON W. DUDAS
*Director of the United States Patent and Trademark Office*